United States Patent
Shao

(10) Patent No.: US 11,851,409 B2
(45) Date of Patent: Dec. 26, 2023

(54) DEUTERATED BENZYLAMINOPYRIMIDINEDIONE DERIVATIVES AND USE THEREOF

(71) Applicant: QINGDAO JI'AO PHARMACEUTICAL TECHNOLOGY CO., LTD, Shandong (CN)

(72) Inventor: Changlun Shao, Shandong (CN)

(73) Assignee: QINGDAO JIÃO PHARMACEUTICAL TECHNOLOGY CO., LTD, Shandong (CN)

(*) Notice: Subject to any disclaimer, the term of this patent is extended or adjusted under 35 U.S.C. 154(b) by 234 days.

(21) Appl. No.: 17/425,408

(22) PCT Filed: Jan. 19, 2020

(86) PCT No.: PCT/CN2020/072904
§ 371 (c)(1),
(2) Date: Jul. 23, 2021

(87) PCT Pub. No.: WO2020/151605
PCT Pub. Date: Jul. 30, 2020

(65) Prior Publication Data
US 2022/0089551 A1    Mar. 24, 2022

(30) Foreign Application Priority Data
Jan. 25, 2019   (CN) .......................... 201910070397.4

(51) Int. Cl.
*C07D 239/545* (2006.01)
*A61P 9/10* (2006.01)
*C07D 405/04* (2006.01)

(52) U.S. Cl.
CPC ............ *C07D 239/545* (2013.01); *A61P 9/10* (2018.01); *C07D 405/04* (2013.01)

(58) Field of Classification Search
CPC ............ C07D 239/545; C07D 239/553; C07D 401/04; C07D 407/04; A61K 31/513
See application file for complete search history.

(56) References Cited

U.S. PATENT DOCUMENTS

| | | | | |
|---|---|---|---|---|
| 6,221,335 B1 * | 4/2001 | Foster | ................. | C07B 59/002 424/1.81 |
| 6,440,710 B1 * | 8/2002 | Keinan | ................. | C12P 13/02 435/188.5 |
| 6,603,008 B1 * | 8/2003 | Ando | ................. | A61P 25/00 546/271.4 |
| 7,517,990 B2 * | 4/2009 | Ito | ................. | C07D 233/56 546/184 |
| 9,181,200 B2 * | 11/2015 | Oslob | ................. | C07D 401/12 |
| 2007/0082929 A1 * | 4/2007 | Gant | ................. | A61P 43/00 546/273.7 |
| 2007/0197533 A1 * | 8/2007 | Zhou | ................. | C07D 401/04 514/249 |
| 2007/0197695 A1 * | 8/2007 | Potyen | ................. | C08K 5/55 524/110 |

FOREIGN PATENT DOCUMENTS

| | | |
|---|---|---|
| CN | 105473576 | 10/2018 |
| EP | 0369627 | 12/1994 |
| WO | 2004014868 | 2/2004 |

OTHER PUBLICATIONS

Beshchasna et al., Recent Advances in Manufacturing Innovative Stents, Pharmaceutics, 12, 349, pp. 1-36 (2020).*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Fura, A., Role of pharmacologically active metabolites in drug discovery and development, DDT, 2006, 11, pp. 133-142.*
Anari et al., Bridging cheminformatic metabolite prediction and tandem mass spectrometry, DDT, 2005, vol. 10, No. 10, pp. 711-717.*
Nedderman, A.N.R., Metabolites in safety testing: Metabolite Identification Strategies in Discovery and Development, Biopharm. Drug Depos. 2009, 30, pp. 153-162.*
Dyck, Journal of Neurochemistry vol. 46 Issue 2, pp. 399-404 (1986).*
Tonn, Biological Mass Spectrometry vol. 22 Issue 11, pp. 633-642 (1993).*
Haskins, Biomedical Spectrometry vol. 9 Issue 7, pp. 269-277 (1982).*
Wolen, Journal of Clinical Pharmacology (1986); 26:419-424.*
Browne, Journal of Clinical Pharmacology (1998); 38:213-220.*
Baillie, Pharmacology Rev.(1981); 33:81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol.(1999); 39:817-825.*
Honma et al., Drug Metab Dispos 15 (4): 551-559 (1987).*
International Search Report and Written Opinion in corresponding PCT/CN2020/072904, dated Apr. 21, 2020.

* cited by examiner

*Primary Examiner* — Deepak R Rao
(74) *Attorney, Agent, or Firm* — Hovey Williams LLP

(57) ABSTRACT

The present invention discloses deuterated benzylaminopyrimidinedione derivatives, the use thereof and the pharmaceutical composition containing the same. They may be used for suppressing the activities of myosin. The present invention also relates to the method of preparing this type of compounds and the pharmaceutical composition, and their use in treatment of hypertrophic cardiomyopathy and related heart diseases.

10 Claims, No Drawings

DEUTERATED BENZYLAMINOPYRIMIDINEDIONE DERIVATIVES AND USE THEREOF

RELATED APPLICATIONS

This application is the U.S. National Stage of International Patent Application No. PCT/CN2020/072904, filed Jan. 19, 2020, incorporated by reference herein in its entirety, which claims the priority benefit of Chinese Patent Application 201910070397.4 filed Jan. 25, 2019.

TECHNICAL FIELD

The present disclosure relates to the technical field of medicine, and specifically to compounds and pharmaceutical compositions for the treatment of hypertrophic cardiomyopathy and related heart diseases, and methods for using the same and use thereof. In particular, the present disclosure relates to deuterated benzylaminopyrimidinedione derivatives which may be used as myosin inhibitors.

BACKGROUND ART

Hypertrophic cardiomyopathy (HCM) is a hereditary myocardial disease characterized by ventricular hypertrophy, ventricular cavity diminution, and left ventricular diastolic compliance decline. The thickness of the ventricular septum or left ventricular wall measured by two-dimensional echocardiography is ≥15 mm, or, with a clear family history of the disease, is ≥13 mm, is usually not accompanied by the enlargement of the left ventricular cavity, and the thickening of the left ventricular wall caused by increased load such as hypertension, aortic stenosis and congenital subaortic membrane should be excluded. Most of them are asymptomatic. The main clinical manifestations are dyspnea and angina pectoris like attacks. Obstructive patients have dizziness, near-syncope, and sudden death.

Hypertrophic cardiomyopathy mainly involves cardiac hypertrophy and increases the weight of the heart. Hypertrophy and disordered arrangement of cardiomyocytes, nuclear malformation, and spiral destruction of fasciculus structure are occurred. Along with the disease development, the myocardial fibrosis composition increases gradually, and may have the thickened coronary artery wall, and the lumen becomes smaller.

Treatment of hypertrophic cardiomyopathy mainly uses the p receptor blocking agents (propranolol, metoprolol), calcium channel blockers (verapamil, diltiazem), IA anti-arrhythmic drugs (disopyramide), and the like, these medicines are not marked as a treatment for HCM, and basically no strict clinical trial evidence can be used to guide clinical use. Currently, there are no marketed drugs for hypertrophic cardiomyopathy.

Myosin is a motor protein in a superfamily. It is a long, asymmetric molecule with the shape of "Y" and the length thereof is about 160 nm. Myosin is a highly asymmetric hexamer composed of two myosin heavy chains (MHC), two essential light chains (ELC) and two regulatory light chains (RLC), which is the main component of thick myofilaments. Myosin is not only an important structural protein and contractile protein in myocardium, but also has the activity of adenosine triphosphatase (ATPase), so it is often called myosin ATPase. The direct energy source for muscle contraction is the hydrolysis of adenosine triphosphate (ATP) by myosin.

Myocardial myosin has become a new strategy for the treatment of heart failure and cardiomyopathy. Myocardial myosin is the most downstream target for regulating myocardial contraction. Drugs acting on this target do not affect intracellular calcium ion concentration, which can effectively increase or decrease myocardial contractility to avoid adverse reactions such as arrhythmia. Myocardial myosin-targeting inhibitors will be an important new method for the treatment of hypertrophic cardiomyopathy. Most studies have consistently shown that myocardial myosin mutations will lead to an increase in cardiac myoconstriction activity. If excessive myoconstriction is a major defect in hypertrophic cardiomyopathy, small-molecule inhibitors of the myotome may ameliorate the disease from its source and may eliminate characteristics of HCM such as hypertrophy, cellular disorder, and myocardial fibrosis.

The purpose of the present disclosure is to provide novel compounds as myosin inhibitors to address the long-term need for improvement and treatment of HCM and associated heart disease.

SUMMARY

The following only outlines some aspects of the present disclosure and is not limited to this. These aspects and other sections are explained more fully below. All references in this specification are quoted herein as a whole. In case of any difference between the disclosed contents of this specification and the quoted references, the disclosed contents of this specification shall prevail.

The present disclosure relates to a novel deuterated benzylaminopyrimidinedione derivatives, which can effectively inhibit the activity of myosin and thus can be used for the preparation of drugs for the treatment of heart failure and cardiomyopathy, especially for the preparation of drugs for the treatment of hypertrophic cardiomyopathy and related heart diseases.

The compound of the present disclosure has stable properties and good safety, and has advantages in pharmacodynamics and pharmacokinetics, such as good bioavailability or good metabolic stability, and the like, so it has a good clinical application prospect.

The present disclosure also provides a method for preparing these compounds and pharmaceutical compositions containing these compounds.

On the one hand, the present disclosure relates to a compound, wherein the compound is the compound represented by Formula I, or a stereoisomer, a geometric isomer, a tautomer, an oxynitride, a hydrate, a solvate, a metabolite, a pharmaceutical acceptable salt or a prodrug of the compound represented by Formula I,

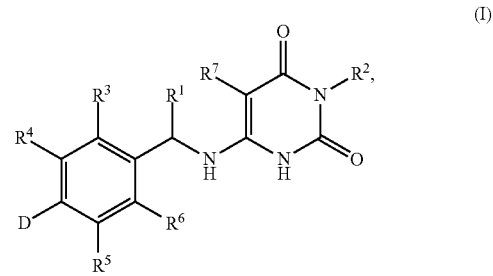

(I)

wherein $R^1$, $R^2$, $R^3$, $R^4$, $R^5$, $R^6$ and $R^7$ possess the meanings described herein.

In some embodiments, $R^1$ is selected from the group consisting of $C_{1-6}$ alkyl, $C_{3-8}$ cycloalkyl, heterocyclyl composed of 3-8 atoms, $C_{6-10}$ aryl and heteroaryl composed of 5-10 atoms, wherein $C_{1-6}$ alkyl, $C_{3-8}$ cycloalkyl, heterocyclyl composed of 3-8 atoms, $C_{6-10}$ aryl and heteroaryl composed of 5-10 atoms are independently not substituted or substituted by 1, 2, 3, or 4 $R^x$, respectively, wherein $R^x$ has the meaning as described herein.

In some embodiments, $R^2$ is selected from the group consisting of $C_{1-6}$ alkyl, $C_{3-8}$ cycloalkyl, heterocyclyl composed of 3-8 atoms, $C_{6-10}$ aryl and heteroaryl composed of 5-10 atoms, wherein $C_{1-6}$ alkyl, $C_{3-8}$ cycloalkyl, heterocyclyl composed of 3-8 atoms, $C_{6-10}$ aryl and heteroaryl composed of 5-10 atoms are independently not substituted or substituted by 1, 2, 3, or 4 $R^y$, respectively, wherein $R^y$ has the meaning as described herein.

In some embodiments, $R^3$, $R^4$, $R^5$ and $R^6$ are each independently selected from the group consisting of H, D, F, Cl, Br, I, CN, $NO_2$, OH, $NH_2$, SH, $C_{1-6}$ alkyl, $C_{1-6}$ haloalkyl, $C_{1-6}$ haloalkoxy, $C_{1-6}$ alkylamino, $C_{1-6}$ alkoxy, —C(=O)$R^g$, —C(=O)$OR^h$, —S(=O)$_2R^g$, —C(=O)$NR^iR^j$, —S(=O)$_2NR^iR^j$, $C_{3-8}$ cycloalkyl, heterocyclyl composed of 3-8 atoms, $C_{6-10}$ aryl and heteroaryl composed of 5-10 atoms, wherein OH, $NH_2$, SH, $C_{1-6}$ alkyl, $C_{1-6}$ haloalkyl, $C_{1-6}$ haloalkoxy, $C_{1-6}$ alkylamino, $C_{1-6}$ alkoxy, $C_{3-8}$ cycloalkyl, heterocyclyl composed of 3-8 atoms, $C_{6-10}$ aryl and heteroaryl composed of 5-10 atoms are independently not substituted or substituted by 1, 2, 3, or 4 $R^z$, respectively, wherein $R^g$, $R^h$, $R^i$, $R^j$ and $R^z$ have the meaning as described herein.

In some embodiments, $R^7$ is selected from the group consisting of H, D, F, Cl, Br, I, $C_{1-6}$ alkyl and $C_{1-6}$ haloalkyl.

In some embodiments, $R^x$, $R^y$ and $R^z$ are each independently selected from the group consisting of D, F, Cl, Br, I, CN, $NO_2$, OH, $NH_2$, SH, $C_{1-6}$ alkyl, $C_{1-6}$ haloalkyl, $C_{1-6}$ alkylamino, $C_{3-8}$ cycloalkyl, heterocyclyl composed of 3-8 atoms, $C_{6-10}$ aryl, heteroaryl composed of 5-10 atoms, —(CR$^aR^b$)$_nR^o$, —OR$^c$, —C(=O)$R^d$, —C(=O)$OR^e$, —S(=O)$_2R^d$, —C(=O)NR$^eR^f$ and —S(=O)$_2NR^eR^f$, wherein $R^o$, $R^a$, $R^b$, $R^c$, $R^d$, $R^e$, $R^f$ and n have the meaning as described herein.

In some embodiments, $R^a$ and $R^b$ are each independently selected from the group consisting of H, $C_{1-6}$ alkyl and $C_{1-6}$ haloalkyl.

In some embodiments, $R^o$ is each independently selected from the group consisting of $C_{3-8}$ cycloalkyl, heterocyclyl composed of 3-8 atoms, $C_{6-10}$ aryl and heteroaryl composed of 5-10 atoms.

In some embodiments, $R^c$, $R^e$, $R^f$, $R^h$, $R^i$ and $R^j$ are each independently selected from the group consisting of H, D, $C_{1-6}$ alkyl, $C_{1-6}$ haloalkyl, $C_{3-8}$ cycloalkyl, heterocyclyl composed of 3-8 atoms, $C_{6-10}$ aryl and heteroaryl composed of 5-10 atoms; or, $R^e$, $R^f$ and the nitrogen atoms attached to them together form a 3-8 atoms of heterocyclyl or a 5-10 atoms of heteroaryl.

In some embodiments, $R^d$ and $R^g$ are each independently selected from the group consisting of H, OH, $NH_2$, $C_{1-6}$ alkyl, $C_{1-6}$ haloalkyl, $C_{1-6}$ alkylamino, $C_{1-6}$ alkoxy, $C_{3-8}$ cycloalkyl, heterocyclyl composed of 3-8 atoms, $C_{6-10}$ aryl and heteroaryl composed of 5-10 atoms.

In some embodiments, n is each independently 1, 2, 3 or 4.

In some embodiments, the compound in the present disclosure is the compound represented by Formula II, or a stereoisomer, a geometric isomer, a tautomer, an oxynitride, a hydrate, a solvate, a metabolite, a pharmaceutical acceptable salt or a prodrug of the compound represented by Formula II,

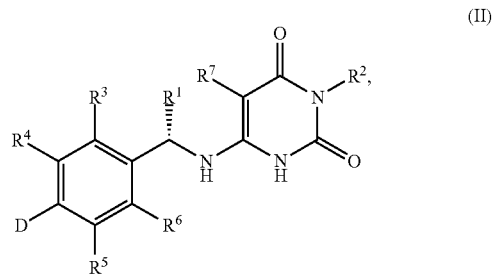

(II)

wherein $R^1$, $R^2$, $R^3$, $R^4$, $R^5$, $R^6$ and $R^7$ have the meaning as described herein.

In some other embodiments, $R^1$ is selected from the group consisting of $C_{1-4}$ alkyl, $C_{3-6}$ cycloalkyl, heterocyclyl composed of 3-6 atoms, phenyl and heteroaryl composed of 5-6 atoms, wherein $C_{1-4}$ alkyl, $C_{3-6}$ cycloalkyl, heterocyclyl composed of 3-6 atoms, phenyl and heteroaryl composed of 5-6 atoms are independently not substituted or substituted by 1, 2, 3, or 4 $R^x$, respectively, wherein $R^x$ has the meaning as described herein.

In some other embodiments, $R^3$, $R^4$, $R^5$ and $R^6$ are each independently selected from the group consisting of H, D, F, Cl, Br, I, CN, $NO_2$, OH, $NH_2$, SH, $C_{1-4}$ alkyl, $C_{1-4}$ haloalkyl, $C_{1-4}$ haloalkoxy, $C_{1-4}$ alkylamino, $C_{1-4}$ alkoxy, —C(=O)$R^g$, —C(=O)$OR^h$, —S(=O)$_2R^g$, —C(=O)$NR^iR^j$, —S(=O)$_2NR^iR^j$, $C_{3-6}$ cycloalkyl, heterocyclyl composed of 3-6 atoms, $C_{6-10}$ aryl and heteroaryl composed of 5-6 atoms, wherein OH, $NH_2$, SH, $C_{1-4}$ alkyl, $C_{1-4}$ haloalkyl, $C_{1-4}$ haloalkoxy, $C_{1-4}$ alkylamino, $C_{1-4}$ alkoxy, $C_{3-6}$ cycloalkyl, heterocyclyl composed of 3-6 atoms, $C_{6-10}$ aryl and heteroaryl composed of 5-6 atoms are independently not substituted or substituted by 1, 2, 3, or 4 $R^z$, respectively, wherein $R^g$, $R^h$, $R^i$, $R^j$ and $R^z$ have the meaning as described herein.

In some other embodiments, $R^7$ is selected from the group consisting of H, D, F, Cl, Br, I, $C_{1-4}$ alkyl and $C_{1-4}$ haloalkyl.

In some other embodiments, $R^2$ is selected from the group consisting of $C_{1-4}$ alkyl, $C_{3-6}$ cycloalkyl, heterocyclyl composed of 3-6 atoms, phenyl and heteroaryl composed of 5-6 atoms, wherein $C_{1-4}$ alkyl, $C_{3-6}$ cycloalkyl, heterocyclyl composed of 3-6 atoms, phenyl and heteroaryl composed of 5-6 atoms are independently not substituted or substituted by 1, 2, 3, or 4 $R^y$, respectively, wherein $R^Y$ has the meaning as described herein.

In some embodiments, $R^1$ is selected from the group consisting of methyl, ethyl, n-propyl, isopropyl, n-butyl, tert-butyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl, wherein methyl, ethyl, n-propyl, isopropyl, n-butyl, tert-butyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl are independently not substituted or substituted by 1, 2, 3, or 4 $R^x$, respectively, wherein $R^x$ has the meaning as described herein.

In some embodiments, $R^3$, $R^4$, $R^5$ and $R^6$ are each independently selected from the group consisting of H, D, F, Cl, Br, I, CN, $NO_2$, OH, $NH_2$, SH, methyl, ethyl, n-propyl, isopropyl, n-butyl, tert-butyl, trifluoromethyl, trifluoromethoxy, methylamino, dimethylamino, methoxyl, ethyoxyl, —C(=O)$R^g$, —C(=O)$OR^h$, —S(=O)$_2R^g$, —C(=O)$NR^iR^j$, —S(=O)$_2NR^iR^j$, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl, wherein OH, $NH_2$, SH, methyl, ethyl, n-propyl, isopropyl, n-butyl, tert-butyl, methylamino, dimethylamino, methoxyl, ethyoxyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl are independently not substituted or substituted by 1, 2, 3, or 4 $R^z$, respectively, wherein $R^g$, $R^h$, $R^i$, $R^j$ and $R^z$ have the meaning as described herein.

In some embodiments, $R^7$ is selected from the group consisting of H, D, F, Cl, Br, methyl, ethyl and propyl.

In some embodiments, $R^2$ is selected from the group consisting of methyl, ethyl, n-propyl, isopropyl, n-butyl, 1-methylpropyl, tert-butyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl, wherein methyl, ethyl, n-propyl, isopropyl, n-butyl, tert-butyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl are independently not substituted or substituted by 1, 2, 3, or 4 $R^y$, respectively, wherein $R^y$ has the meaning as described herein.

In some other embodiments, $R^x$, $R^y$ and $R^z$ are each independently selected from the group consisting of D, F, Cl, Br, I, CN, $NO_2$, OH, $NH_2$, —SH, $C_{1-4}$ alkyl, $C_{1-4}$ haloalkyl, $C_{1-4}$ alkylamino, $C_{3-6}$ cycloalkyl, heterocyclyl composed of 3-6 atoms, phenyl, heteroaryl composed of 5-6 atoms, —$(CR^aR^b)_nR^0$, —$OR^c$, —C(=O)$R^d$, —C(=O)$OR^c$, —S(=O)$_2R^d$, —C(=O)$NR^eR^f$ and —S(=O)$_2NR^eR^f$, wherein $R^0$, $R^a$, $R^b$, $R^c$, $R^d$, $R^e$, $R^f$ and n have the meaning as described herein.

In some other embodiments, $R^a$ and $R^b$ are each independently selected from the group consisting of H, $C_{1-4}$ alkyl and $C_{1-4}$ haloalkyl.

In some other embodiments, $R^0$ is each independently selected from the group consisting of $C_{3-6}$ cycloalkyl, heterocyclyl composed of 3-6 atoms, phenyl and heteroaryl composed of 5-6 atoms.

In some other embodiments, $R^c$, $R^e$, $R^f$, $R^h$, $R^i$ and $R^j$ are each independently selected from the group consisting of H, D, $C_{1-4}$ alkyl, $C_{1-4}$ haloalkyl, $C_{3-6}$ cycloalkyl, heterocyclyl composed of 3-6 atoms, phenyl and heteroaryl composed of 5-6 atoms; or, $R^e$, $R^f$ and the nitrogen atoms attached to them together form a 3-6 atoms of heterocyclyl or a 5-6 atoms of heteroaryl.

In some other embodiments, $R^d$ and $R^g$ are each independently selected from the group consisting of H, OH, $NH_2$, $C_{1-4}$ alkyl, $C_{1-4}$ haloalkyl, $C_{1-4}$ alkylamino, $C_{1-4}$ alkoxy, $C_{3-6}$ cycloalkyl, heterocyclyl composed of 3-6 atoms, phenyl and heteroaryl composed of 5-6 atoms.

In some other embodiments, $R^X$, $R^Y$ and $R^z$ are each independently selected from the group consisting of D, F, Cl, Br, I, CN, $NO_2$, OH, $NH_2$, —SH, methyl, ethyl, n-propyl, isopropyl, n-butyl, tert-butyl, trifluoromethyl, difluoromethyl, methylamino, dimethylamino, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl or pyridazinyl, —$(CR^aR^b)_nR^0$, —$OR^c$, —C(=O)$R^d$, —C(=O)$OR^c$, —S(=O)$_2R^d$, —C(=O)$NR^eR^f$ and —S(=O)$_2NR^eR^f$, wherein $R^0$, $R^a$, $R^b$, $R^c$, $R^d$, $R^e$, $R^f$ and n have the meaning as described herein.

In some embodiments, $R^a$ and $R^b$ are each independently selected from the group consisting of H, methyl, ethyl, n-propyl, isopropyl, n-butyl, tert-butyl and trifluoromethyl.

In some embodiments, $R^0$ is each independently selected from the group consisting of cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl.

In some embodiments, $R^c$, $R^e$, $R^f$, $R^h$, $R^i$ and $R^j$ are each independently selected from the group consisting of H, D, methyl, ethyl, n-propyl, isopropyl, n-butyl, tert-butyl, trifluoromethyl, difluoromethyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl; or, $R^e$, $R^f$ and the nitrogen atoms attached to them together form a 3-6 atoms of heterocyclyl or a 5-6 atoms of heteroaryl.

In some embodiments, $R^d$ and $R^g$ are each independently selected from the group consisting of H, OH, $NH_2$, methyl, ethyl, n-propyl, isopropyl, n-butyl, tert-butyl, trifluoromethyl, difluoromethyl, methylamino, dimethylamino, methoxyl, ethyoxyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl.

In some other embodiments, the compound in the present disclosure is the compound in one of following structures, or a stereoisomer, a geometric isomer, a tautomer, an oxynitride, a hydrate, a solvate, a metabolite, a pharmaceutical acceptable salt or a prodrug of the compound in one of following structures.

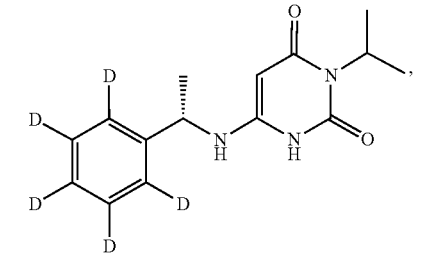

001

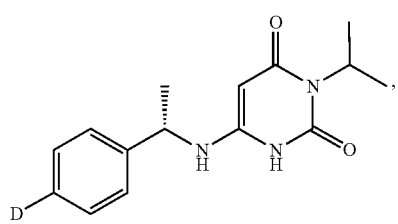

002

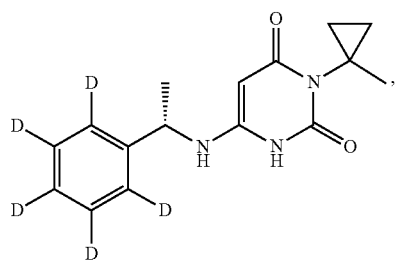

003

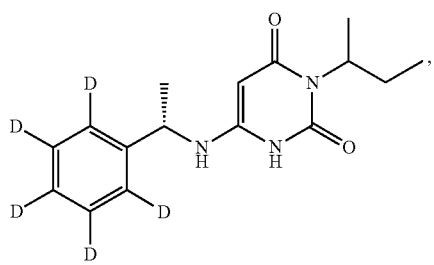

004

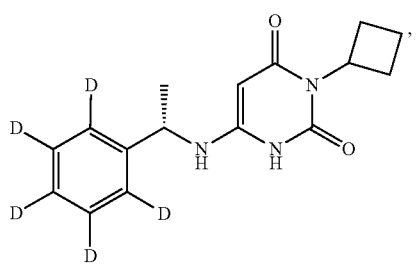

005

-continued

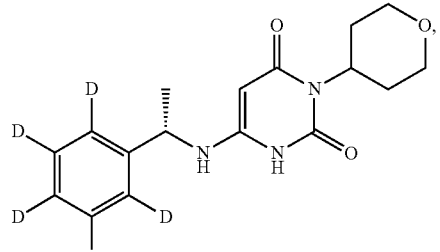

006

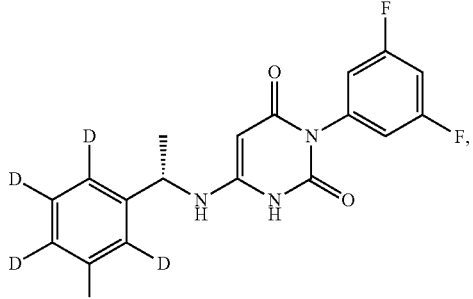

007

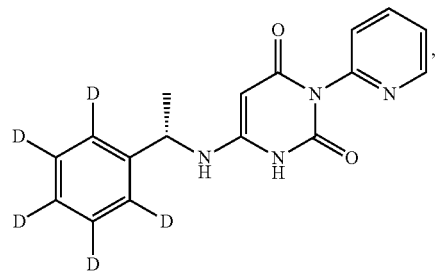

008

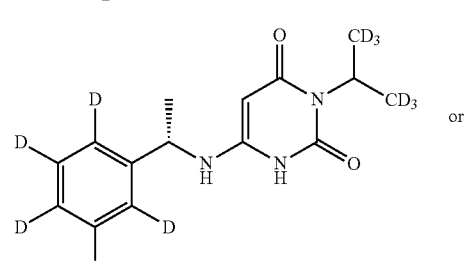

009 or

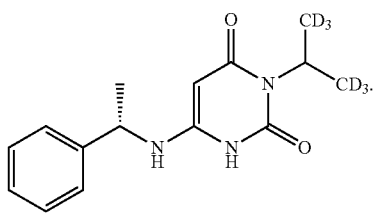

010

On the other hand, the present disclosure relates to a pharmaceutical composition comprising a compound disclosed herein. In some embodiments, the pharmaceutical composition to which the present disclosure relates further comprises a pharmaceutically acceptable excipient, carrier, adjuvant or any combination thereof.

On the other hand, the present disclosure relates to use of the compound or the pharmaceutical composition disclosed herein in the preparation of a drug, wherein the drug is used to prevent, treat or alleviate hypertrophic cardiomyopathy or cardiac diseases with pathophysiological characteristics associated with hypertrophic cardiomyopathy.

On the other hand, the present disclosure relates to use of the compound or the pharmaceutical composition disclosed herein in the preparation of a drug, wherein the drug is used to prevent, treat or alleviate diastolic heart failure, ischemic heart disease, angina or restrictive cardiomyopathy with ejection fraction retention.

On the other hand, the present disclosure relates to use of the compound or the pharmaceutical composition disclosed herein in the preparation of a drug, wherein the drug is used to inhibit myosin.

On the other hand, the present disclosure relates to methods for the preparation, separation and purification of compounds shown in formula (I) or (II).

The biological test results show that the compound of the present disclosure has a good inhibitory effect on myosin, especially myocardial myosin, so the compound provided by the present disclosure can be used as a good myosin inhibitor.

Any embodiment of any aspect of the disclosure may be combined with other embodiments so long as they do not contradict each other. In addition, in any embodiment of any aspect of the disclosure, any of the technical features may be applicable to the technical features in other embodiments so long as they do not contradict each other.

The foregoing outlines only certain aspects of the present disclosure, but is not limited to them. These and other aspects will be described in more detail and completeness below.

Definitions and General Terms

Some embodiments of the disclosure are now described in detail, their examples are illustrated by the attached structural and chemical formulae. The disclosure is intended to cover all alternatives, modifications and equivalent technical solutions, which are included within the scope of the disclosure as defined in the claim. Technicians in the field shall be aware that many methods and materials similar or equivalent to the present disclosure can be used in the practice of the present disclosure. The disclosure is by no means limited to the methods and materials mentioned herein. In the event that one or more documents, patents and similar materials combined differ from or contradict this disclosure (including but not limited to the terms defined, the application of the terms, the technology described, and the like), this disclosure shall prevail.

It should be further recognized that certain features of the present disclosure are described in multiple independent embodiments for the purpose of being clearly visible, but may also be provided in a combination form in a single embodiment. On the contrary, the characteristics of the present disclosure are described in a single embodiment for the sake of brevity, but may also be provided separately or in any appropriate sub-combination.

Unless otherwise stated, the following definitions used herein shall be applied. For the purposes of the present disclosure, the chemical elements are consistent with the periodic table CAS edition and the Handbook of Chemistry and Physics, 75th edition, 1994. In addition, general principles of organic chemistry can be referred to the description in "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are incorporated by reference into the present disclosure.

The articles "a", "an (one)" and "the" used herein are intended to include "at least one" or "one or more" unless otherwise stated or unless there is a clear conflict in the context. Thus, the articles used herein refer to articles with one or more (i.e., at least one) object. For example, "one component" means one or more components, that is, more than one component may be considered for adoption or use in the implementation of the embodiment.

The term "patient" used herein refers to a person (including adults and children) or other animals. In some embodiments, a "patient" is a person.

The term "stereoisomer" refers to compounds that has the same chemical structure but the atoms or groups are arranged differently in space. Stereoisomers include enantiomers, diastereomers, conformational isomers (rotational isomers), geometric (cis/trans) isomers, hindered rotation isomers, and the like.

The term "tautomer" or "tautomeric form" refers to structural isomers with different energies that can be converted into each other through low energy barriers. If tautomerism is possible (for example, in a solution), a chemical equilibrium of tautomers can be achieved. For example, protontautomer (also known as prototropic tautomer) includes interconversion achieved by proton migration, such as keto-enol isomerization and imine-enamine isomerization.

"pharmaceutically acceptable" refers to such compounds, raw materials, combination and/or dosage forms, they are suitable for contacting with the patient tissue without excessive toxicity, irritation, allergic reaction or other problems corresponding to reasonable benefit/risk ratio and complications in the range of reasonable medical judgment, and effectively using in the intended use.

The term "substituted" means that one or more hydrogen atoms in a given structure are replaced by a specific substituent group. Unless otherwise indicated, an optional substituent group may be substituted at various replaceable positions of the group. The term "optionally substituted by . . . " and the term "not substituted or substituted by . . . " can be used interchangeably, that is, the structure is not substituted or is substituted by one or a plurality of substituents of the present disclosure, wherein the "a plurality of" means 1, 2, 3, 4 or more, but not exceeding the number of sites where the structure may be substituted. When the structure is substituted by a plurality of substituents, the plurality of substituents may be the same or different substituent groups. In detail, the substituent in the present disclosure includes, but is not limited to, D, F, Cl, Br, I, $N_3$, —CN, —$NO_2$, —$NH_2$, —OH, —SH, —COH, —$CONH_2$, —C(=O)$NHCH_3$, —C(=O)N(CH$_3$)$_2$, —C(=O)-alkyl, —C(=O)-alkoxy, alkyl, alkoxy, sulphanyl, alkylamino, alkenyl, alkynyl, haloalkyl, haloalkoxy, hydroxyl-substituted alkyl, cycloalkyl, heterocyclyl, aryl, heteroaryl, and the like.

In each part of this specification, substituents of compounds disclosed herein are disclosed according to group types or ranges. In particular, the disclosure includes each independent sub-combination of each member of these group types and ranges. For example, the term "$C_1$-$C_6$ alkyl" refers specifically to methyl, ethyl, $C_3$ alkyl, $C_4$ alkyl, $C_5$ alkyl and $C_6$ alkyl that are independently disclosed.

In each part of the disclosure, a linking substituent is described. When the structure clearly requires a linker (linking group), the Markus variable enumerated for that group should be understood as a linker. For example, if the structure requires a linker and the Markush group definition for that variable enumerates an "alkyl" or "aryl", it should be understood that the "alkyl" or "aryl" represents the linked alkylene groups or arylidene groups, respectively.

The terms "halogen" and "halogenate" are used interchangeably herein to refer to fluorine (F), chlorine (Cl), bromine (Br) or iodine (I).

The term "alkyl" or "alkyl group" used herein refers to a saturated linear or branched monovalent hydrocarbon group containing 1-20 carbon atoms, wherein the alkyl group may optionally be substituted by one or more substituents described herein. In some embodiments, the alkyl group contains 1-6 carbon atoms. In other embodiments, the alkyl group contains 1-4 carbon atoms. In some embodiments, the alkyl group contains 1-3 carbon atoms.

Some non-limiting examples of alkyl groups comprise methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), and the like.

The term "alkoxyl" means that the alkyl group is connected to the rest of the molecule by oxygen atoms, where the alkyl group has the meaning described in the present disclosure. Unless otherwise specified in detail, the alkoxy groups described herein contain 1-12 carbon atoms. In some embodiments, the alkoxy group contains 1-6 carbon atoms. In some other embodiments, the alkoxy group contains 1-4 carbon atoms. In some other embodiments, the alkoxy group contains 1-3 carbon atoms. The alkoxy groups may optionally be substituted by one or more substituents described herein.

Some non-limiting examples of alkoxy groups comprise methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), and the like.

The term "alkylamino" or "alkyl amino" includes "N-alkylamino" and "N,N-dialkylamino", which refers to amino groups independently substituted with one or two alkyl groups, respectively, wherein the alkyl group has the meaning as described herein. Suitable alkyl amino groups can be monoalkylamino or dialkylamino. Some non-limiting examples comprise N-methylamino, N-ethylamino, N,N-dimethylamino, N,N-diethylamino and the like. The alkylamino group is optionally substituted with one or more substituents described herein.

The term "haloalkyl", or "haloalkoxy" refers to an alkyl group or alkoxy group substituted with one or more halogen atoms, wherein the alkyl and alkoxy groups have the meanings described in the present disclosure. Some non-limiting examples comprise trifluoromethyl, trifluoromethoxy, and the like.

In some embodiments, $C_1$-$C_6$ haloalkyls contain fluorine-substituted $C_1$-$C_6$ alkyls. In some other embodiments, $C_1$-$C_4$ haloalkyls contain fluorine-substituted $C_1$-$C_4$ alkyls. In some embodiments, $C_1$-$C_2$ haloalkyls contain fluorine-substituted $C_1$-$C_2$ alkyls.

The term "cycloalkyl" refers to a monovalent or multivalent non-aromatic saturated monocyclic, bicyclic or tricyclic system containing 3-12 carbon atoms.

In some embodiments, the cycloalkyl group contains 3-12 carbon atoms; in some other embodiments, the cycloalkyl group contains 3-8 carbon atoms; in some embodiments, the cycloalkyl group contains 3-6 carbon atoms. Some non-limiting examples of cycloalkyl groups comprise cyclopropyl, cyclobutyl, cyclopentyl, cyclohexyl, and the like. The cycloalkyl group is optionally substituted with one or more substituents described herein.

The term "heterocycle", "heterocyclyl", or "heterocyclic" as used interchangeably herein refers to a monovalent or multivalent, monocyclic, bicyclic, or tricyclic system containing 3-14 ring atoms in which one or more ring atoms are independently substituted by heteroatom with a meaning as described herein, and ring can be completely saturated or contains one or more units of unsaturation, but not aromatic ring. In some embodiments, the "heterocycle", "heterocyclyl", or "heterocyclic" group is a 3-8-membered monocycle composed of 3 to 8 atoms (2 to 7 carbon atoms and 1 to 3 heteroatoms selected from N, O, P or S, wherein the S or P is optionally substituted with one or more oxygen atoms to provide the groups such as SO, SO$_2$, PO or PO$_2$), or a 7-12-membered bicycle (4 to 9 carbon atoms and 1 to 3 heteroatoms selected from N, O, P or S, wherein the S or P is optionally substituted with one or more oxygen atoms to provide the groups such as SO, SO$_2$, PO or PO$_2$). The heterocyclic groups are optionally substituted by one or more of the substituents described herein. The heterocyclyl may be a carbon group or heteroatom group, wherein the —CH$_2$— groups of the ring can optionally be replaced by —C(=O)—, the sulfur atoms of the ring can optionally be oxidized to S-oxide, and the nitrogen atoms of the ring can optionally be oxidized to N-oxide. Some non-limiting examples of heterocyclyl comprise epoxyethyl, azacyclobutyl, oxacyclobutyl, thiocyclobutyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxycyclopentyl, dithiocyclopentyl, tetrahydropyranyl, dihydropyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, and the like. Examples in which the —CH$_2$— group in the heterocyclyl is replaced by —C(=O)— include, but are not limited to, 2-oxopyrrolidinyl, oxo-1,3-thiazolidinyl, 2-piperidonyl, 3,5-dioxopiperidinyl, pyrimidindionyl, and the like. Examples in which the sulfur atom in the heterocyclyl is oxidized include, but are not limited to, sulfolanyl, thiomorpholinyl 1,1-dioxide, and the like. The heterocyclyl group is optionally substituted with one or more substituents described herein.

The term "aryl" refers to monocyclic, bicyclic, and tricyclic carbocyclic ring systems containing 6 to 14 ring atoms, or 6 to 12 ring atoms, or 6 to 10 ring atoms, wherein at least one ring system is aromatic, wherein each ring system contains a ring composed of 3 to 7 atoms and has one or more points of attachment to link to the rest of the molecule. The term "aryl" may be used interchangeably with the term "aryl ring". Examples of aryl groups can comprise phenyl, naphthyl, and anthracyl. The aryl group is optionally substituted by one or more of the substituents described herein.

The term "heteroaryl" or "heteroaromatic ring" means a monovalent or multivalent monocyclic, bicyclic or tricyclic ring system containing 5-14 ring atoms, or 5-10 ring atoms, or 5-6 ring atoms, wherein at least one ring is aromatic and at least one ring contains one or more heteroatoms. The heteroaryl group is usually, but not necessarily, linked to the parent molecule through the aromatic ring of the heteroaryl group. The term "heteroaryl" can be used interchangeably with the terms "heteroaromatic ring" or "heteroaromatic compound". The heteroaryl group is optionally substituted with one or more substituents described in the present disclosure. In some embodiments, the heteroaryl composed of 5-10 atoms contains 1, 2, 3, or 4 heteroatoms independently selected from O, S, and N; in some other embodiments, the heteroaryl composed of 5-6 atoms is a monocyclic ring system and contains 1, 2, 3, or 4 heteroatoms independently selected from O, S and N. Some non-limiting examples of heteroaryl groups comprise pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl or pyridazinyl; and non-limiting examples also comprise the following bicyclic rings: benzimidazolyl, benzofuranyl, benzothienyl, indolyl, quinolinyl, isoquinolinyl, and the like.

The term "composed of j atoms" or "j-membered", wherein j is an integer, typically describes the number of atoms forming a ring in a molecule, and the number of atoms forming a ring in the molecule is j. For example, piperidinyl is a heterocycle (heterocyclic ring) composed of 6 atoms or 6-membered heterocycle, and cyclohexyl is a cycloalkyl composed of 6 atoms or 6-membered cycloalkyl.

The term "unsaturated" used herein refers to a group having one or more degrees of unsaturation.

The term "heteroatom" refers to O, S, N, P, and Si, including any oxidized forms of N, S, and P; the forms of primary amine, secondary amine, tertiary amine and quaternary ammonium; or the form that the hydrogen atom of nitrogen atom of a heterocyclic ring is substituted, for example, N (as N in 3,4-dihydro-2H-pyrrolyl), NH (as NH in pyrrolidinyl) or NR (as NR in N-substituted pyrrolidinyl, wherein R is the substituent described herein).

The term "prodrug" used herein refers to a compound that is transformed in vivo into a compound of formula (I) or (II). Such a transformation can be affected by hydrolysis of the prodrug in blood or enzymatic transformation of the prodrug to the parent form in blood or tissue. Prodrugs of the compounds disclosed herein may be esters. In existing inventions, esters that may be utilized as prodrugs are phenyl esters, aliphatic ($C_{1-24}$) esters, acyloxymethyl esters, carbonates, carbamates, and amino acid esters. For example, a compound disclosed herein that contains an OH group may be acylated to obtain a compound in its prodrug form. Other prodrug forms comprise phosphates, for example, those phosphate compounds resulting from the phosphonation of an OH group on the parent.

A "metabolite" is a product produced through metabolism in the body of a specified compound or salt thereof. Metabolites of a compound may be identified using routine techniques known in the art and their activities may be characterized using tests such as those described herein. Such products may result from the oxidation, reduction, hydrolysis, amidation, deamidation, esterification, deesterification, enzymatic cleavage, and the like, of the administered compound. Accordingly, the present disclosure comprises metabolites of compounds, including metabolites produced by contacting a compound disclosed herein with a mammal for a period of time sufficiently.

A "pharmaceutically acceptable salts" used in the present disclosure refer to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. The pharmaceutically acceptable nontoxic salts formed by acids comprise, but are not limited to, inorganic acid salts formed by reaction with amino group, including hydrochloride, hydrobromide, phosphate, sulfate and perchlorate, and organic acid salts formed by reaction with amino group, such as acetate, oxalate, maleate, tartarate, citrate, succinate and malonate, or salts obtained by using other methods used in the art such as ion exchange. This disclosure also envisions the quaternary ammonium salt formed by any N-containing groups of the compounds. Water-soluble or oil-soluble or dispersible products may be obtained by quaternization. Pharmaceutically acceptable salts further comprise appropriate and nontoxic ammonium, quaternary ammonium salt, and amine cations formed against ionization equilibrium, such as halide, hydroxide, carboxylate, sulfate, phosphate, nitrate, $C_1$-$C_8$ sulfonate or aryl sulfonate.

A "solvate" in the present disclosure refers to a complex formed by one or more solvent molecules with a compound disclosed herein. The solvents that form solvates comprise, but are not limited to, water, isopropanol, ethanol, methanol, dimethylsulfoxide (DMSO), ethyl acetate, acetic acid, ethanolamine or a mixture thereof. The term "hydrate" refers to the complex where the solvent molecule is water.

The term "treatment" as used in the present disclosure for any disease or condition, in some embodiments, refers to ameliorating the disease or condition (i.e., slowing or preventing or alleviating the development of the disease or at least one of its clinical symptoms). In some other embodiments, "treatment" refers to alleviating or improving at least one physical parameter, including physical parameters that may not be perceived by the patient. In some other embodiments, "treatment" refers to the regulation of a disease or condition physically (for example, stabilizing perceptible symptoms) or physiologically (for example, stabilizing physical parameters) or both. In some other embodiments, "treating" refers to preventing or delaying the onset, occurrence, or worsening of a disease or condition.

The term "therapeutic efficacious dose" means that when administered to a subject to treat a disease, the amount of the compound is sufficient for the treatment of the disease. The "therapeutic efficacious dose" can vary with the compound, the disease and severity, and the condition, age, weight, sex, and the like, of the subject to be treated.

The compound, its pharmaceutically acceptable salt, pharmaceutical preparation and its composition in the present disclosure can be used as selective 5-hydroxytryptamine (5-HT) reuptake inhibitors, and have potential for the treatment of human central nervous system dysfunction, especially affective disorders. The affective disorder includes, but is not limited to, depression, anxiety disorder, social phobia, obsessive-compulsive disorder, panic attack, specific phobia, agoraphobia, mania, panic disorder and post-traumatic stress disorder.

Unless otherwise specified, all suitable isotopic changes, stereoisomers, tautomers, solvates, metabolites, salts and pharmaceutically acceptable prodrugs of the compounds of the present disclosure are included in the scope of the present disclosure.

In the structure disclosed herein, when the stereochemistry of any specific chiral atom is not specified, all stereoisomers of the structure are considered in the present disclosure and are included in the present disclosure as the compound disclosed in the present disclosure. When stereochemistry is indicated by a solid wedge or dashed line that represents a specific configuration, then the stereoisomers of the structure are clear and defined.

The compounds of the present disclosure may exist in the form of salts. In some embodiments, the salt refers to a pharmaceutically acceptable salt. The term "pharmaceutically acceptable" means that the substance or composition must be chemically and/or toxicologically compatible with the other ingredients of the preparation and/or the mammals to which it is administered. In some other embodiments, the salt is not necessarily a pharmaceutically acceptable salt, and may be an intermediate for preparing and/or purifying the compound of the present disclosure and/or for separating the enantiomers of the compound of the present disclosure.

Any structural formula given in the present disclosure is also intended to represent the non-isotopically enriched forms and isotopically enriched forms of these compounds. The isotope-enriched compound has the structure described by the general formula given in the present disclosure, except that one or more atoms are replaced by atoms having the selected atomic weight or mass number. Exemplary isotopes that can be introduced into the compounds of the present disclosure include isotopes of hydrogen, carbon, nitrogen, oxygen, phosphorus, sulfur, fluorine, and chlorine, such as $^{2}H$, $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$ and $^{125}I$.

On the other hand, the present disclosure relates to preparation of an intermediate of a compound shown in formula (I) or (II).

Pharmaceutical Compositions, Formulations and Administration of Compounds of the Present Disclosure The pharmaceutical composition disclosed herein includes a compound of formula (I) or (II) or its individual stereoisomer, racemic or non-racemic mixture of isomer or its pharmaceutically acceptable salts or solvates. In some embodiments of the present disclosure, the pharmaceutical composition further comprises at least one pharmaceutically acceptable carrier, adjuvant or excipient, and, optionally, other therapeutic and/or preventive components.

Suitable carriers, adjuvants and excipients are well known to those skilled in the art and are described in detail, for example, in Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C., Handbook of Pharmaceutical Excipients (2005) Pharmaceutical Press, Chicago.

It should also be recognized that when used in therapy, certain compounds of the present disclosure may exist in free form or, if appropriate, in the form of pharmaceutically acceptable derivatives thereof. Some non-limiting embodiments of pharmaceutically acceptable derivatives include pharmaceutically acceptable prodrugs, salts, esters, and salts of these esters, or any additional adducts or derivatives capable of directly or indirectly providing the compound of the present disclosure or its metabolites or residues when administered to patients in need.

Suitable pharmaceutically acceptable excipients will vary depending on the specific dosage form selected. In addition, pharmaceutically acceptable excipients can be selected according to their specific functions in the composition. Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, corrigents, taste masking agents, colorant, anti-caking agents, humectants, chelating agents, plasticizers, tackifiers, antioxidants, preservatives, stabilizers, surfactants and buffers. Technicians may recognize that certain pharmaceutically acceptable excipients can provide more than one function and provide alternative functions, depending on how many these excipients are present in the preparation and what other excipients are present in the preparation.

The pharmaceutical composition disclosed in the present disclosure is prepared using techniques and methods known to those skilled in the art. A description of some common methods in the art can be found in Remington's Pharmaceutical Sciences (Mack Publishing Company).

Therefore, on the other hand, the present disclosure relates to a process for preparing a pharmaceutical composition comprising a compound disclosed in the present disclosure and a pharmaceutically acceptable excipient, carrier, adjuvant, solvent or a combination thereof, wherein the process comprises mixing various ingredients. The pharmaceutical composition containing the compound disclosed in the present disclosure can be prepared by mixing, for example, at ambient temperature and atmospheric pressure.

The compounds disclosed in the present disclosure are usually formulated into a dosage form suitable for administration to a patient through a desired route. For example, dosage forms include those suitable for the following routes of administration: (1) oral administration, such as tablets, capsules, caplets, pills, lozenges, powders, syrups, elixirs, suspensions, solutions, emulsions, sachets and cachets; (2) parenteral administration, such as sterile solutions, suspensions and reconstituted powders; (3) transdermal administration, such as transdermal patches; (4) rectal administration, such as suppositories; (5) inhalation, such as aerosols, solutions and dry powders; and (6) topical administration, such as creams, ointments, lotions, solutions, pastes, sprays, foams and gels.

In some embodiments, the compounds disclosed herein can be formulated into oral dosage forms. In some other embodiments, the compounds disclosed herein can be formulated into inhaled dosage forms. In some other embodiments, the compounds disclosed herein can be formulated into dosage forms for transnasal administration. In some other embodiments, the compounds disclosed herein can be formulated into dosage forms for transdermal administration. In some embodiments, the compounds disclosed herein can be formulated into dosage forms for topical administration.

The pharmaceutical composition provided herein may be provided as a pressed tablet, a developed tablet, a chewable pastille, a fast dissolving tablet, a recompression tablet, or an enteric-coated tablet, icing tablet or film coating tablet.

The pharmaceutical composition provided herein may be provided in soft or hard capsules, which may be prepared from gelatin, methyl cellulose, starch or calcium alginate.

The pharmaceutical composition provided herein may be administered parenterally by injection, infusion or implantation for topical or systemic administration. Parenteral administration as used in the present disclosure includes intravenous, intraarterial, intraperitoneal, intrathecal, intraventricular, intraurethral, intrasternal, intracranial, intramuscular, intrasynovial and subcutaneous administration.

The pharmaceutical composition provided herein can be formulated into any dosage form suitable for parenteral administration, including solutions, suspensions, emulsions, micelles, liposomes, microspheres, nano-systems and solid forms suitable for preparation of solutions or suspensions in liquids prior to injection. Such dosage forms can be prepared according to conventional methods known to those skilled in the art of pharmaceutical science (see Remington: The Science and Practice of Pharmacy, ibid).

According to the disease to be treated and the state of the subject, the compound or its pharmaceutically acceptable salt described herein can be administered in the following ways: oral, parenteral (for example, intramuscular, intraperitoneal, intravenous, ICV, intrapool injection or infusion, subcutaneous injection or implantation), implantation (for example, when the compound or pharmaceutical salt is connected to the stent device), inhalation spray, nasal, vaginal, rectal, sublingual or topical administration, and can be formulated separately or together in appropriate dosage unit preparations containing conventional non-toxic pharmaceutical carriers, adjuvants and vehicles suitable for each route of administration.

In the treatment or prevention of ventricular diastolic conditions that require improvement during diastole, the appropriate dosage level will usually be about 0.001 to 100 mg/kg patient body weight/day, which can be administered in a single dose or in multiple doses. In some embodiments, the dosage level will be about 0.01 to about 25 mg/kg/day; in some embodiments, about 0.05 to about 10 mg/kg/day. A suitable dosage level may be about 0.01 to 25 mg/kg/day, about 0.05 to 10 mg/kg/day, or about 0.1 to 5 mg/kg/day. Within this range, the dosage may be 0.005 to 0.05, 0.05 to 0.5, or 0.5 to 5.0 mg/kg/day. In some embodiments, for oral administration, the composition is provided in the following tablet form: containing 1.0 to 1000 milligrams of active ingredient, specifically containing 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0 and 1000.0 milligrams of active ingredients, so as to adjust the treatment given to the patient to be treated for symptoms. The compound or pharmaceutically acceptable salt may be administered in a regimen of 1 to 4 times a day, and in some embodiments, may be administered in a regimen of one or two times a day.

The compound or pharmaceutical composition disclosed herein can be administered simultaneously with, or before or after, one or more other therapeutic agents. The compound or pharmaceutical composition disclosed herein and other therapeutic agents can be administered separately through the same or different administration routes, or they can be administered in the same pharmaceutical composition form. When the compound or pharmaceutical composition provided herein is used simultaneously with one or more other therapeutic agents, it is preferably a pharmaceutical composition containing the other drugs in addition to the compound or pharmaceutical composition provided herein. Therefore, the pharmaceutical composition provided herein includes those pharmaceutical compositions that contain one or more other active ingredients or therapeutic drugs in addition to the compound or pharmaceutical composition provided herein. Appropriate other active drugs include: drugs that slow the progression of heart failure by down-regulating the neurohormonal stimulation of the heart and try to prevent heart remodeling (for examples, ACE inhibitors, angiotensin receptor blockers (ARB), blockers, aldosterone receptor antagonists or neuroendopeptidase inhibitors); drugs that improve cardiac function by stimulating cardiac contractility (for examples, positive inotropic drugs such as adrenergic agonist dobutamine or phosphodiesterase inhibitor milrinone); and drugs that reduce cardiac preload (for example, diuretic such as furosemide) or drugs that reduce cardiac afterload (any type of vasodilators, including but not limited to calcium channel blockers, phosphodiesterase inhibitors, endothelin receptor antagonists, renin inhibitors or smooth muscle myosin modulators). The weight ratio of the compound provided herein to the second active ingredient is variable and will depend on the effective dose of each ingredient. Generally, an effective dose of each ingredient will be used.

Uses of the Compound and Pharmaceutical Composition of the Present Disclosure

The compounds or their pharmaceutically acceptable salts and pharmaceutical compositions provided herein may be used for the preparation of drugs for the prevention, treatment or mitigation of heart disease in mammals, including humans, or for the preparation of drugs for the inhibition of myosin.

In particular, the amount of compounds in the compound or its pharmaceutically acceptable salt and pharmaceutical composition herein can effectively and detectably selectively inhibit myosin, especially myocardial myosin. The compounds or their pharmaceutically acceptable salts and pharmaceutical compositions herein may be used as drugs for the treatment of human heart failure and cardiomyopathy, in particular hypertrophic cardiomyopathy and heart diseases with pathophysiological characteristics associated with hypertrophic cardiomyopathy.

The compounds or their pharmaceutically acceptable salts and pharmaceutical compositions herein can be applied to, but not limited to, administration of the effective dose of the compounds or their pharmaceutically acceptable salts or pharmaceutical compositions herein to patients to prevent, treat or relieve hypertrophic cardiomyopathy and heart diseases with pathophysiological characteristics associated with hypertrophic cardiomyopathy.

The compound of the present disclosure or a pharmaceutically acceptable salt thereof is also used to treat diastolic heart failure, ischemic heart disease, angina or restrictive cardiomyopathy with ejection fraction retention. The compound of the present disclosure or a pharmaceutically acceptable salt thereof can also promote beneficial ventricular remodeling of left ventricular hypertrophy caused by volume or pressure overload, such as chronic mitral regurgitation, chronic aortic stenosis, or chronic systemic hypertension. The compound or its pharmaceutically acceptable salt is aimed at correcting or reducing the main cause of volume or pressure overload (valve repair/replacement, effective antihypertensive therapy). By reducing the left ventricular filling pressure, the compound of the present disclosure or a pharmaceutically acceptable salt thereof can reduce the risk of pulmonary edema and respiratory failure; reducing or eliminating functional mitral regurgitation and/or reducing left atrium pressure can reduce the risk of suddenness or persistent atrial fibrillation, and it reduces the concomitant risk of arterial thromboembolic complications including but not limited to cerebral artery embolic stroke; reducing or eliminating dynamic and/or static left ventricular outflow tract obstruction can reduce the possibility of requiring interval ablation treatment (surgical or percutaneous) and its concomitant risks of short- and long-term complications. The compound of the present disclosure or a pharmaceutically acceptable salt thereof can reduce the severity of the chronic ischemic state associated with HCM, and thereby reduce the risk of sudden cardiac death (SCD) or its equivalent diseases in patients with an implantable cardioversion device-defibrillator (frequent and/or repeated ICD discharge) and/or reduce the need for potentially toxic antiarrhythmic drugs. The compound of the present disclosure or a pharmaceutically acceptable salt thereof may be valuable in reducing or eliminating the need for concurrent drugs (with their attendant potential toxicity, drug-drug interaction, and/or side effects). The compound of the present disclosure or a pharmaceutically acceptable salt thereof can reduce interstitial myocardial fibrosis and/or slow the progression of left ventricular hypertrophy, prevent or reverse left ventricular hypertrophy.

In addition to being beneficial to the treatment of human beings, the compounds and pharmaceutical compositions of the present disclosure may also be applied to veterinary treatment of mammals in pets, introduced species of animals and farm animals. Other examples of animals include horses, dogs, and cats. Here, the compounds of the present disclosure include their pharmaceutically acceptable derivatives.

General Synthetic Procedures

Examples are listed below to describe the present disclosure. However, it needs to be understood that the present disclosure is not limited to these examples, but merely provides a method for the practice of the present disclosure.

Generally, the compounds disclosed herein may be prepared by methods described herein, wherein the substituents are as defined for formula (I) or (II), except further noted. The following reaction solutions and examples are presented to further exemplify the contents of present disclosure.

Persons skilled in the art will recognize that the chemical reactions described in the present disclosure may be adapted to prepare a number of other compounds disclosed herein, and alternative methods for preparing the compounds disclosed herein are deemed to be within the scope disclosed herein. For example, the synthesis of non-exemplified compounds according to the present disclosure may be successfully performed by modifications by those skilled in the art, e.g., by appropriately protecting interfering groups, by utilizing other known reagents other than those described herein, or by making routine modifications for reaction conditions. In addition, the reactions or known reaction conditions disclosed herein will be recognized as having applicability for preparing other compounds disclosed herein.

In the examples described below, unless otherwise indicated, all temperatures are set forth in degrees Celsius. Reagents were purchased from commercial suppliers such as Aldrich Chemical Company, Arco Chemical Company and Alfa Chemical Company, and were used without further purification unless otherwise indicated. Common reagents were purchased from Shantou XiLong Chemical Factory, Guangdong Guanghua Reagent Chemical Factory Co. Ltd., Guangzhou Reagent Chemical Factory, Tianjin FuYu Fine Chemical Co. Ltd., Tianjin Fuchen Reagent Chemical Factory, Wuhan Xinhuayuan Technology Development Co. Ltd., Qingdao Tenglong Reagent Chemical Co. Ltd., and Qingdao Ocean Chemical Factory.

Anhydrous tetrahydrofuran, dioxane, toluene, and ether were obtained by refluxing and drying with metal sodium. Anhydrous dichloromethane and chloroform were obtained by refluxing and drying with calcium hydride. Ethyl acetate, petroleum ether, hexane, N,N-dimethyl acetamide and N,N-dimethyl formamide were dried by anhydrous sodium sulfate prior to use.

The reactions set forth below were done generally under a positive pressure of nitrogen or argon or with a drying tube (unless otherwise stated) provided on anhydrous solvents, and the reaction flasks were typically fitted with suitable rubber stopper for the introduction of substrates via syringe. Glassware was dried.

Chromatographic column used a silica gel column. Silica gel (300-400 mesh) was purchased from Qingdao Ocean Chemical Factory.

$^1$H NMR spectra were recorded with a Bruker 400 MHz or 600 MHz nuclear magnetic resonance spectrometer. $^1$H NMR spectra were obtained by using CDCl$_3$, DMSO-d$_6$, CD$_3$OD or acetone-d$_6$ as solvents (ppm as unit), using TMS (0 ppm) or chloroform (7.26 ppm) as the reference standard. When multiplet was reported, the following abbreviations were used: s (singlet), d (doublet), t (triplet), m (multiplet), br (broadened), brs (broadened singlet), dd (doublet of doublets), and dt (doublet of triplets). Coupling constants J are reported in Hertz (Hz).

The following abbreviations are used throughout the disclosure:

| PPTS | pyridinium p-toluenesulfonate | DMSO-d$_6$ | Deuterated Dimethyl Sulfoxide |
|---|---|---|---|
| PE | petroleum ether | mmol, mM | millimole |
| EA | ethyl acetate | μM | micromole |
| TLC | thin-layer chromatography | mg | milligram |
| Rt | retention time | g | gram |
| CDCl$_3$ | Deuterochloroform | kg | kilogram |
| DMSO | Dimethyl Sulfoxide | mL, ml | milliliter |

The following synthetic scheme describes the steps for preparing the disclosed compound of the present disclosure, unless otherwise stated, wherein R$^1$, R$^2$, R$^3$, R$^4$, R$^5$, R$^6$ and R$^7$ each have the definition described herein, M is C$_{1-4}$ alkyl.

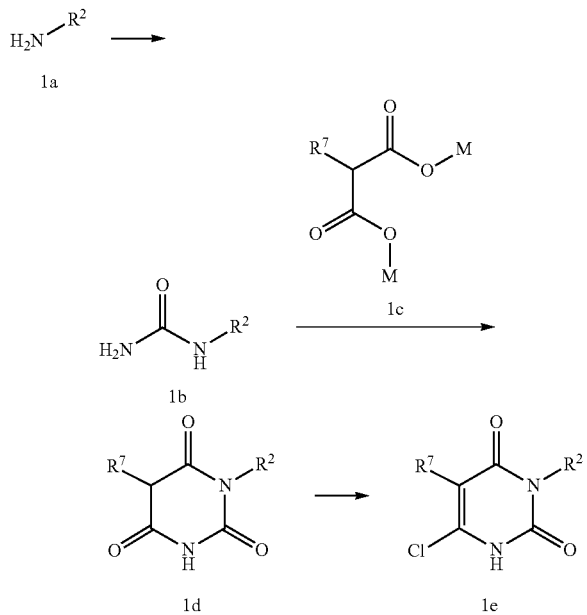

Synthesis scheme 1

The intermediate compound 1e can be prepared by the method described in the synthesis scheme 1. The specific synthesis process is as follows.

Compound 1b can be obtained by reacting compound 1a with isocyanates in the solvent. The solvents used in the reaction include but are not limited to dichloromethane, and the like.

Compound 1d can be obtained by ring-closing compound 1b in alcohols in the presence of malonates 1c substituted by different R$^7$ and bases (including but not limited to sodium methylate). The alcohols used in the reaction include but are not limited to methanol.

Compound 1e can be obtained by reacting compound 1 d with phosphorus oxychloride in the presence of phase transfer catalyst (including but not limited to triethyl benzyl chloride amine, and the like).

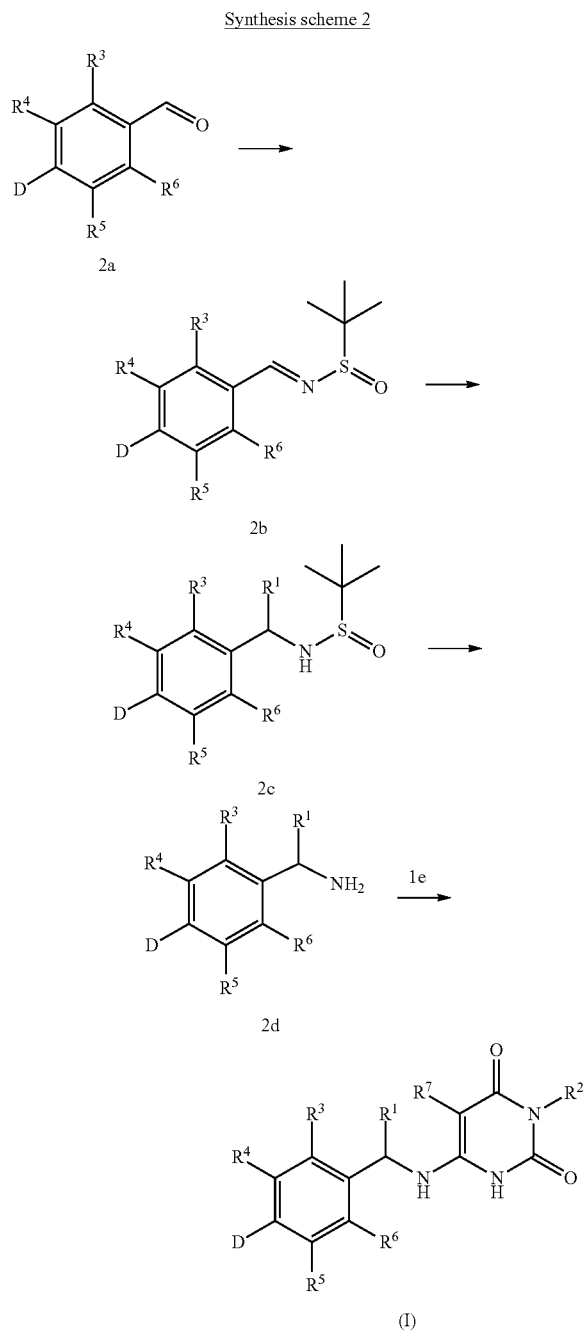

The compound (1) can be prepared by the method described in the synthesis scheme 2. The specific synthesis process is as follows.

Compound 2b can be obtained by reacting compound 2a with 2-methyl-2-propane sulfenamide and copper salts (including but not limited to anhydrous copper sulfate, and the like) in solvent. The solvents used in the reaction include but are not limited to dichloromethane, and the like.

Compound 2c can be obtained by addition reaction of compound 2b with Grignard reagents substituted by different R¹. The solvents used in the reaction include but are not limited to tetrahydrofuran, and the like.

Compound 2d can be obtained by stirring compound 2c in organic solution of hydrogen chloride (including but not limited to 1,4-dioxane solution, and the like). The solvents used in the reaction include but are not limited to methanol, and the like.

Compound (1) can be obtained by substitution reaction of compound 2d with compound 1e in solvent. The solvents used in the reaction include but are not limited to 1,4-dioxane, and the like.

The compounds, pharmaceutical compositions and their use provided herein are further explained below in combination with examples.

EXAMPLE

Example 1

(S)-3-isopropyl-6-((1-(phenyl-d5)ethyl)amino)pyrimidine-2,4(1H,3H)-dione

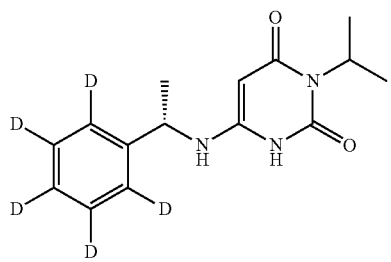 [SMILES: [2H]c1c([2H])c([2H])c([C@H](C)Nc2cc(=O)n(C(C)C)c(=O)[nH]2)c([2H])c1[2H]]

Step 1: (R)-2-methyl-N-((phenyl-d5)methylene) propane-2-sulfinamide

Under the protection of nitrogen, benzaldehyde-2,3,4,5,6-d5 (3 g, 26.99 mmol) was added into the dichloromethane (200 mL) mixing system of (R)-2-methyl propane-2-sulfinamide (4.91 g, 40.48 mmol), PPTS (339.12 mg, 1.35 mmol) and magnesium sulfate (16.24 g, 134.95 mmol). The mixture was stirred overnight at room temperature. TLC monitored that the reaction was complete, the insoluble substance was filtered and removed. The filter cake was washed with dichloromethane (50 mL), the filtrate was concentrated, and the residue was purified by silica gel column chromatography (PE/EA (v/v)=20/1), and 3 g of the pale yellow solid title compound was obtained, with a yield of 51.8%.

Step 2: (R)-2-methyl-N—((S)-1-(phenyl-d5)ethyl) propane-2-sulfinamide

Under the protection of nitrogen, (R)-2-methyl-N-((phenyl-d5)methylene)propane-2-sulfinamide (3 g, 14 mmol) was dissolved in anhydrous tetrahydrofuran (50 mL). The methylmagnesium bromide (28 mL, 28 mmol, 1 M) solution was slowly dropped into the resulting reaction solution when its temperature is decreased to −50° C. After that, it was slowly raised to room temperature and stirred overnight. The reaction solution was cooled by ice bath, then saturated ammonium chloride solution was slowly dropped therein to quench the reaction, the resultant was separated, the aqueous phase was extracted with ethyl acetate (50 mL×2), the organic phase was combined, dried with anhydrous sodium sulfate, filtered and concentrated, and the residue was purified by silica gel column chromatography (PE/EA (v/v)=2/1) to obtain a yellow oil-like title compound of 1.4 g, with a yield of 43.4%.

Step 3: (S)-1-(phenyl-d5)ethane-1-amine Hydrochloride

The solution of 1, 4-dioxane with hydrogen chloride (3.04 mL, 12.16 mmol) was added into the solution of methanol (20 mL) with the (R)-2-methyl-N—((S)-1-(phenyl-d5)ethyl) propane-2-sulfinamide (1.4 g, 6.08 mmol). The reaction mixture was stirred for 1 hour at room temperature, then decompressed out most of the solvent, the residue was dissolved in methanol (3 mL), then added with the ether (100 mL). The obtained system was continued to stir overnight, and a large number of white solids were precipitated. After filtration, the filter cake was washed with ether (20 mL) and dried at reduced pressure to obtain a white solid title compound of 800 mg, with a yield of 81%.

Step 4: (S)-3-isopropyl-6-((1-(phenyl-d5)ethyl) amino)pyrimidine-2,4(1H,3H)-dione Sodium hydroxide solution (20 mL, 1 M) was added to (S)-1-(phenyl-d5)ethane-1-amine hydrochloride (388.1 mg, 2.39 mmol) and the mixture was stirred for 30 min. Then the mixture was extracted with ethyl acetate (50 mL×2), dried with anhydrous sodium sulfate, filtered, and concentrated at reduced pressure. The obtained residue was added to a solution of 6-chloro-3-isopropyl pyrimidine-2,4(1H,3H)-dione (300 mg, 1.59 mmol) (referring to CN105473576A, the synthetic route of compound 1.3) and 1,4-dioxane (10 mL). The reaction system was heated to 100° C. and stirred overnight. After the reaction was stopped and the reaction system was naturally cooled to room temperature, it was concentrated at reduced pressure. The obtained residue was purified by silica gel column chromatography (PE/EA (v/v)=1/1), and 48 mg of white solid title compound was obtained with a yield of 10.8%.

MS (ESI, pos.ion) m/z: 279.2 [M+1]$^+$;

$^1$H NMR (400 MHz, DMSO-d$_6$) δ 9.80 (s, 1H), 6.53 (d, J=6.0 Hz, 1H), 4.96-4.84 (m, 1H), 4.54-4.45 (m, 1H), 4.34 (s, 1H), 1.40 (d, J=6.7 Hz, 3H), 1.27 (d, J=6.8 Hz, 6H).

EE value was 96.3%. Detection condition: chiral chromatographic column Chiralpak IC, 250 mm×4.6 mm×5 μm, eluent was a mixing solution of 13% ethanol and 87% n-hexane at a flow rate of 1.0 mL/min, Rt=8.807 min, 266 nm.

Example 2

(S)-3-isopropyl-6-((1-(phenyl-4-d)ethyl)amino)pyrimidine-2,4(1H,3H)-dione

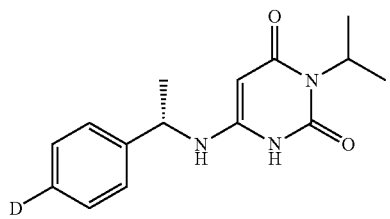 [SMILES: [2H]c1ccc([C@H](C)Nc2cc(=O)n(C(C)C)c(=O)[nH]2)cc1]

Step 1: (R)-2-methyl-N-((phenyl-4-d)methylene) propane-2-sulfinamide

Under the protection of nitrogen, the dichloromethane (200 mL) solution of benzaldehyde-4-d (0.7 g, 6.53 mmol), (R)-2-methyl propane-2-sulfinamide (1.58 g, 13.07 mmol) and anhydrous copper sulfate (3.13 g, 19.60 mmol) was stirred overnight at room temperature. The insoluble substance was filtered and removed with diatomite. The filter cake was washed with dichloromethane (50 mL), the filtrate was concentrated, and the residue was purified by silica gel column chromatography (PE/EA (v/v)=20/1), and 0.8 g of the pale yellow solid title compound was obtained, with a yield of 58.4%.

Step 2: (R)-2-methyl-N—((S)-1-(phenyl-4-d)ethyl) propane-2-sulfinamide

Under the protection of nitrogen, (R)-2-methyl-N-((phenyl-4-d) methylene) propane-2-sulfinamide (0.8 g, 3.8 mmol) was dissolved in anhydrous dichloromethane (20 mL). The methylmagnesium bromide (7.6 mL, 7.6 mmol, 1 M) solution was slowly dropped into the resulting reaction solution when the temperature was decreased to −60° C. After that, it was slowly raised to room temperature and stirred overnight. The reaction solution was cooled by ice bath, then saturated ammonium chloride solution was slowly dropped therein to quench the reaction, the solution was separated, the aqueous phase was extracted with ethyl acetate (20 mL×2), the organic phase was combined, dried with anhydrous sodium sulfate, filtered and concentrated, and the residue was purified by silica gel column chromatography (PE/EA (v/v)=2/1) to obtain a white solid title compound of 0.8 g with a yield of 92.9%.

Step 3: (S)-1-(phenyl-4-d)ethane-1-amine Hydrochloride

The solution of 1, 4-dioxane with hydrogen chloride (1.9 mL, 7.6 mmol) was added into the solution of methanol (20 mL) with the (R)-2-methyl-N—((S)-1-(phenyl-4-d)ethyl) propane-2-sulfinamide (0.8 g, 3.5 mmol). The reaction mixture was stirred for 1 hour at room temperature, then decompressed out most of the solvent, the residue was dissolved in methanol (1 mL), then added with the ether (50 mL). The obtained system was continued to stir overnight, and a large number of white solids were precipitated. After filtration, the filter cake was washed with ether (20 mL) and dried at reduced pressure to obtain a white solid title compound of 500 mg, with a yield of 90%.

Step 4: (S)-3-isopropyl-6-((1-(phenyl-4-d)ethyl) amino)pyrimidine-2,4(1H,3H)-dione Sodium hydroxide solution (20 mL, 1 M) was added to (S)-1-(phenyl-4-d)ethyl-1-amine hydrochloride (403.7 mg, 2.54 mmol) and the mixture was stirred for 30 min. Then the mixture was extracted with ethyl acetate (50 mL×2), dried with anhydrous sodium sulfate, filtered, and concentrated at reduced pressure. The obtained residue was added to a solution of 6-chloro-3-isopropyl pyrimidine-2,4(1H,3H)-dione (400 mg, 2.12 mmol) and 1,4-dioxane (10 mL). The reaction system was heated to 100° C. and stirred overnight. After the reaction was stopped and the reaction system was naturally cooled to room temperature, it was concentrated at reduced pressure. The obtained residue was purified by silica gel column chromatography (PE/EA (v/v)=1/1), and 81 mg of pale yellow solid title compound was obtained with a yield of 13.9%.

MS (ESI, pos.ion) m/z: 275.3 [M+1]$^+$;

$^1$H NMR (400 MHz, DMSO-d$_6$) δ 9.79 (s, 1H), 7.38-7.32 (m, 4H), 6.52 (d, J=6.4 Hz, 1H), 4.97-4.84 (m, 1H), 4.55-4.44 (m, 1H), 4.34 (s, 1H), 1.40 (d, J=6.7 Hz, 3H), 1.27 (d, J=6.9 Hz, 6H).

Example 3 (S)-3-(3,5-difluorophenyl)-6-((1-(phenyl-d5) ethyl) amino) pyrimidine-2,4(1H,3H)-dione

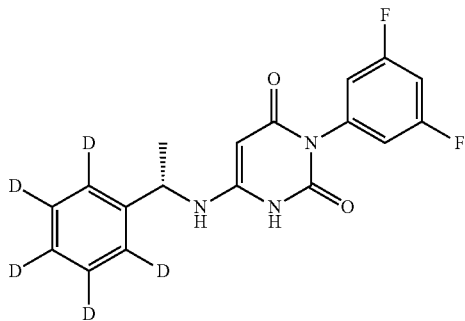 [SMILES: [2H]c1c([2H])c([2H])c([C@H](C)Nc2cc(=O)n(-c3cc(F)cc(F)c3)c(=O)[nH]2)c([2H])c1[2H]]

Step 1: 1-(3,5-difluorophenyl) urea

The trimethylsilyl isocyanate (4.45 g, 38.73 mmol) was slowly dropped into the dichloromethane (100 mL) solution of 3,5-difluoroaniline (5 g, 38.73 mmol) at room temperature. The obtained reaction solution was stirred overnight at room temperature. The reaction solution was cooled to 0° C. and the methanol (40 mL) was slowly dropped therein for quenching reaction. The obtained reaction solution was stirred for 1 hour after rising to room temperature, and then concentrated under the reduced pressure. The obtained residue was stirred overnight with methanol/ether at room temperature and filtered to obtain a yellow solid title compound of 3.2 g, with a yield of 48%.

Step 2: 1-(3,5-difluorophenyl) pyrimidine-2,4,6(1H,3H,5H)-trione

At room temperature, the methanol solution of sodium methoxide (8.02 mL, 40.08 mmol) and dimethyl propionate (1.77 g, 13.36 mmol) was added into the methanol (40 mL) solution of the 1-(3,5-difluorophenyl) urea (2.3 g, 13.36 mmol), the obtained reaction solution was heated to 65° C. and stirred overnight, after natural cooling to room temperature, the water was added therein for quenching reaction, the obtained reaction solution was decompressed out most of methanol. The aqueous phase was adjusted to acidity with 1 M hydrochloric acid (pH=2) and extracted with ethyl acetate (30 mL×2). The organic phase was combined, dried with anhydrous sodium sulfate, filtered and concentrated. The obtained residue was purified by silica gel column chromatography (PE/EA (v/v)=2/1) to obtain the white solid title compound of 1.2 g, with a yield of 37.4%.

Step 3: 6-chloro-3-(3,5-difluorophenyl) pyrimidine-2,4(1H,3H)-dione

Phosphorus oxychloride (10 mL) was added into 1-(3,5-difluorophenyl)pyrimidine-2,4,6(1H,3H,5H)-trione (1.2 g, 5 mmol) and triethyl benzyl ammonium chloride (1.1 g, 5 mmol), the obtained reaction solution reacted at 50° C. for 3 hours, and then was concentrated under the reduced pressure. The residue was poured into ice water, stirred violently for 30 minutes, and then extracted by ethyl acetate (30 mL×2). The organic phase was combined, dried with anhydrous sodium sulfate, filtered and concentrated, and the obtained residue was purified by silica gel column chromatography (PE/EA (v/v)=2/1) to obtain a white solid title compound of 700 mg, with a yield of 54.2%.

Step 4: (S)-3-(3,5-difluorophenyl)-6-((1-(phenyl-d5) ethyl)amino)pyrimidine-2,4(1H,3H)-dione Sodium hydroxide solution (20 mL, 1 M) was added into (S)-1-(phenyl-d5)ethane-1-amine hydrochloride (301.93 mg, 1.86 mmol) and stirred for 30 min. The reaction solution was extracted by ethyl acetate (30 mL×2), dried by anhydrous sodium sulfate, filtered, and concentrated under the reduced pressure. The obtained residue was added to a solution of 6-chloro-3-(3,5-difluorophenyl) pyrimidine-2,4 (1H,3H)-dione (400 mg, 1.55 mmol) and 1,4-dioxane (10 mL), and the reaction system was risen to 100° C. and stirred overnight. After the reaction was stopped and the reaction system was naturally cooled to room temperature, it was concentrated at reduced pressure. The obtained residue was purified by silica gel column chromatography (PE/EA (v/v) =1/1) to obtain a white solid title compound of 50 mg with a yield of 9.3%.

MS (ESI, pos.ion) m/z: 349.2 [M+1]$^+$;

$^1$H NMR (400 MHz, DMSO-d$_6$) δ 10.28 (s, 1H), 7.26 (t, J=9.4 Hz, 1H), 7.08-6.99 (m, 2H), 6.78 (d, J=6.3 Hz, 1H), 4.67-4.56 (m, 1H), 4.53 (s, 1H), 1.45 (d, J=6.7 Hz, 3H).

Example 4

(S)-6-((1-(phenyl-d5)ethyl)amino)-3-(tetrahydro-2H-pyran-4-yl)pyrimidine-2,4(1H,3H)-dione

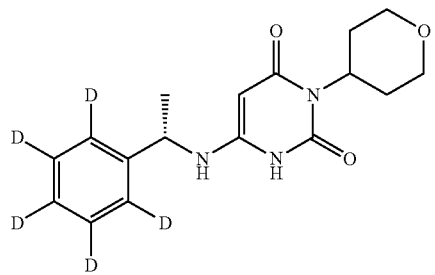 [SMILES: [2H]c1c([2H])c([2H])c([C@H](C)Nc2cc(=O)n(C3CCOCC3)c(=O)[nH]2)c([2H])c1[2H]]

Sodium hydroxide solution (20 mL, 1 M) was added into (S)-1-(phenyl-d5)ethane-1-amine hydrochloride (338.53 mg, 2.08 mmol) and stirred for 30 min. The reaction solution was extracted by ethyl acetate (30 mL×2), dried by anhydrous sodium sulfate, filtered, and concentrated under the reduced pressure. The obtained residue was added to a solution of 6-chloro-3-(tetrahydro-2H-pyran-4-yl) pyrimidine-2,4(1H,3H)-dione (400 mg, 1.73 mmol) (referring to CN105473576A, the synthetic route of compound 9.3) and 1,4-dioxane (10 mL), and the reaction system was risen to 100° C. and stirred overnight. After the reaction was stopped and the reaction system was naturally cooled to room temperature, it was concentrated at reduced pressure. The obtained residue was purified by silica gel column chromatography (PE/EA (v/v)=1/1) to obtain a white solid title compound of 70 mg, with a yield of 12.6%.

MS (ESI, pos.ion) m/z: 321.2 [M+1]$^+$;

$^1$H NMR (400 MHz, DMSO-d$_6$) δ 9.89 (s, 1H), 6.59 (s, 1H), 4.83-4.69 (m, 1H), 4.57-4.47 (m, 1H), 4.38 (s, 1H), 3.97-3.80 (m, 2H), 3.28 (t, J=12.1 Hz, 2H), 2.59-2.51 (m, 2H), 1.40 (d, J=6.7 Hz, 3H), 1.31 (d, J=11.6 Hz, 2H).

Example 5

(S)-6-((1-phenylethyl)amino)-3-(propane-2-yl-1,1,1,3,3,3-d6)pyrimidine-2,4 (1H,3H)-dione

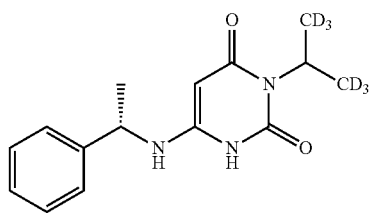 [SMILES: [2H]C([2H])([2H])C(n1c(=O)cc(N[C@@H](C)c2ccccc2)[nH]c1=O)C([2H])([2H])[2H]]

Step 1: 1-(propane-2-yl-1,1,1,3,3,3-d6) Urea

Under the protection of nitrogen, the trimethylsilyl isocyanate (1.25 g, 10.83 mmol) was slowly dropped into the dichloromethane (20 mL) solution of propane-1,1,1,3,3,3-d6-2-amine hydrochloride (1 g, 9.84 mmol) and triethylamine (1.37 mL, 9.84 mmol). The obtained reaction solution was stirred overnight at room temperature. The reaction solution was cooled to 0° C. and the methanol (10 mL) was slowly dropped therein for quenching reaction. The obtained reaction solution was stirred for 1 hour after rising to room temperature, and then concentrated under the reduced pressure. The obtained residue was beaten with methanol/ether (1:40) and filtered to obtain a white solid title compound of 1 g, with a yield of 94.4%.

Step 2: 1-(propane-2-yl-1,1,1,3,3,3-d6) pyrimidine-2,4,6(1H,3H,5H)-trione

At room temperature, the methanol solution of sodium methoxide (4.62 mL, 23.11 mmol) and dimethyl malonate (1.28 g, 9.71 mmol) was added into the methanol (30 mL) solution of the 1-(propane-2-yl-1,1,1,3,3,3-d6) urea (1 g, 9.24 mmol), the obtained reaction solution was heated to 65° C. and stirred overnight, after natural cooling to room temperature, the water was added for quenching reaction, the obtained reaction solution was decompressed out most of methanol. The aqueous phase was adjusted to acidity with 1 M hydrochloric acid (pH=2) and extracted with ethyl acetate (30 mL×2). The organic phase was combined, dried with anhydrous sodium sulfate, filtered and concentrated to obtain the white solid title compound of 1.0 g, with a yield of 61.3%.

Step 3: 6-chloro-3-(propane-2-yl-1,1,1,3,3,3-d6) pyrimidine-2,4(1H,3H)-dione

Phosphorus oxychloride (10 mL) was added into the solution of 1-(propane-2-yl-1,1,1,3,3,3-d6)pyrimidine-2,4,6 (1H,3H,5H)-trione (1.0 g, 5.68 mmol) and triethyl benzyl ammonium chloride (1.29 g, 5.68 mmol), the obtained reaction solution reacted at 50° C. for 3 hours, and then was concentrated under the reduced pressure. The residue was poured into ice water, stirred violently for 30 minutes, and then extracted by ethyl acetate (30 mL×2). The organic phase was combined, dried with anhydrous sodium sulfate, filtered and concentrated, and the obtained residue was purified by silica gel column chromatography (PE/EA (v/v) =2/1) to obtain a pale yellow solid title compound of 300 mg, with a yield of 27.3%.

Step 4: (S)-6-((1-phenylethyl)amino)-3-(propane-2-yl-1,1,1,3,3,3-d6)pyrimidine-2,4(1H,3H)-dione In a 1,4-dioxane (10 mL) solution of (S)-1-phenylethane-1-amine (373.55 mg, 3.08 mmol) and 6-chloro-3-(propane-2-yl-1,1,1,3,3,3-d6) pyrimidine-2,4(1H,3H)-dione (300 mg, 1.54 mmol), the reaction system was heated to 100° C. and stirred overnight. After the reaction was stopped and the reaction system was naturally cooled to room temperature, it was concentrated at reduced pressure. The obtained residue was purified by silica gel column chromatography (PE/EA (v/v)=1/1) to obtain a white solid title compound of 45 mg, with a yield of 10.4%.

MS (ESI, pos.ion) m/z: 280.2 [M+1]$^+$;

$^1$H NMR (400 MHz, DMSO-d$_6$) δ 9.78 (s, 1H), 7.39-7.32 (m, 4H), 7.26 (t, J=6.6 Hz, 1H), 6.51 (d, J=6.6 Hz, 1H), 4.87 (s, 1H) 4.55-4.44 (m, 1H), 4.34 (s, 1H), 1.40 (d, J=6.7 Hz, 3H).

Example 6

3-(sec-butyl)-6-(((S)-1-(phenyl-d5)ethyl)amino)pyrimidine-2,4(1H,3H)-dione

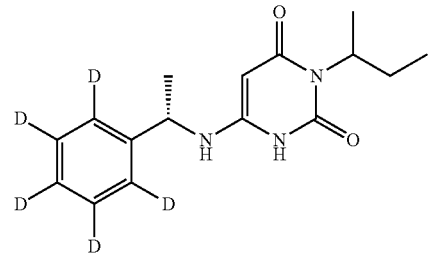 [SMILES: [2H]c1c([2H])c([2H])c([C@H](C)Nc2cc(=O)n(C(C)CC)c(=O)[nH]2)c([2H])c1[2H]]

Step 1: 1-(sec-butyl) Urea

The trimethylsilyl isocyanate (9.25 g, 68.36 mmol) was slowly dropped into the dichloromethane (100 mL) solution of butyl-2-amine (5 g, 68.36 mmol) at room temperature. The obtained reaction solution was stirred overnight at room temperature. The reaction solution was cooled to 0° C. and methanol (40 mL) was slowly dropped therein for quenching reaction. The obtained reaction solution was stirred for 1 hour after rising to room temperature, and then concentrated under the reduced pressure. The obtained residue was stirred overnight with methanol/ether at room temperature and filtered to obtain a white solid title compound of 5.5 g, with a yield of 69.2%.

Step 2: 1-(sec-butyl) pyrimidine-2,4,6(1H,3H,5H)-triketone

At room temperature, the methanol solution of sodium methoxide (28.41 mL, 142.04 mmol) and dimethyl malonate (5.41 mL, 47.35 mmol) was added into the methanol (40 mL) solution of the 1-(sec-butyl) urea (5.5 g, 47.35 mmol), the obtained reaction solution was heated to 65° C. and stirred overnight, after natural cooling to room temperature, the water was added for quenching reaction, the obtained reaction solution was decompressed out most of methanol. The aqueous phase was adjusted to acidity with 1 M hydrochloric acid (pH=2) and extracted with ethyl acetate (30 mL×2). The organic phase was combined, dried with anhydrous sodium sulfate, filtered and concentrated to obtain the yellow solid title compound crude product of 8.4 g with a yield of 96.3%, which was directly put into the next step.

Step 3: 3-(sec-butyl)-6-chloro pyrimidine-2,4(1H,3H)-dione

Phosphorus oxychloride (50 mL) was added into the solution of 1-(sec-butyl)pyrimidine-2,4,6(1H,3H,5H)-trione (8.4 g, 45.6 mmol) and triethyl benzyl ammonium chloride (14.54 g, 63.85 mmol), the obtained reaction solution reacted at 50° C. for 3 hours, and then was concentrated under the reduced pressure. The residue was poured into ice water, stirred violently for 30 minutes, and then extracted by ethyl acetate (30 mL×2). The organic phase was combined, dried with anhydrous sodium sulfate, filtered and concentrated, and the obtained residue was purified by silica gel column chromatography (PE/EA (v/v)=2/1) to obtain a white solid title compound of 2.8 g, with a yield of 30.3%.

Step 4: 3-(sec-butyl)-6-(((S)-1-(phenyl-d5)ethyl)amino)pyrimidine-2,4(1H,3H)-dione Sodium hydroxide solution (20 mL, 1 M) was added into (S)-1-(phenyl-d5)ethane-1-amine hydrochloride (361.25 mg, 2.22 mmol) and stirred for 30 min. The reaction solution was extracted by ethyl acetate (30 mL×2), dried by anhydrous sodium sulfate, filtered, and concentrated under the reduced pressure. The obtained residue was added to a solution of 3-(sec-butyl)-6-chloro pyrimidine-2,4(1H,3H)-dione (300 mg, 1.48 mmol) and 1,4-dioxane (10 mL), the reaction system was heated to 100° C. and stirred overnight. After the reaction was stopped and the reaction system was naturally cooled to room temperature, it was concentrated at reduced pressure. The obtained residue was purified by silica gel column chromatography (PE/EA (v/v)=1/1) to obtain a pale yellow solid title compound of 77 mg, with a yield of 17.78%.

MS (ESI, pos.ion) m/z: 293.2 [M+1]$^+$;

$^1$H NMR (400 MHz, DMSO-d$_6$) δ 9.79 (s, 1H), 6.53 (s, 1H), 4.66 (s, 1H), 4.55-4.44 (m, 1H), 4.34 (s, 1H), 1.97-1.85 (m, 1H), 1.65-1.54 (m, 1H), 1.40 (d, J=6.7 Hz, 3H), 1.24 (d, J=6.8 Hz, 3H), 0.75-0.65 (m, 3H).

Example 7

(S)-3-cyclobutyl-6-((1-(phenyl-d5)ethyl)amino)pyrimidine-2,4(1H,3H)-dione

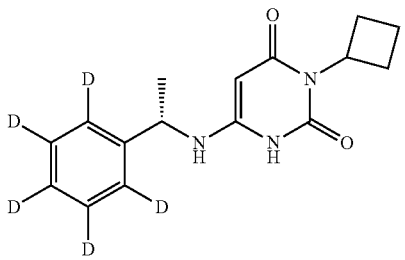 [SMILES: [2H]c1c([2H])c([2H])c([C@H](C)Nc2cc(=O)n(C3CCC3)c(=O)[nH]2)c([2H])c1[2H]]

Step 1: 1-cyclobutylurea

Cyclobutylamine (5 g, 70.3 mmol) was dissolved in dichloromethane (100 mL) at room temperature and slowly dropped into trimethylsilyl isocyanate (9.52 g, 70.3 mmol). The obtained reaction solution was stirred overnight at room temperature. The reaction solution was cooled to 0° C. and methanol (40 mL) was slowly dropped therein for quenching reaction. The obtained reaction solution was stirred for 1 hour after rising to room temperature, and then concentrated under the reduced pressure. The obtained residue was stirred overnight with methanol/ether at room temperature and filtered to obtain a white solid title compound of 6.5 g, with a yield of 81%.

Step 2: 1-(cyclobutyl) pyrimidine-2,4,6(1H,3H,5H)-trione

At room temperature, the methanol solution of sodium methoxide (28.47 mL, 142.36 mmol) and dimethyl malonate (6.83 mL, 59.79 mmol) was added into the methanol (40 mL) solution of the 1-cyclobutylurea (6.5 g, 56.94 mmol), the obtained reaction solution was heated to 65° C. and stirred overnight, after natural cooling to room temperature, the water was added for quenching reaction, the obtained reaction solution was decompressed out most of methanol. The aqueous phase was adjusted to acidity with 1 M hydrochloric acid (pH=2) and extracted with ethyl acetate (30 mL×2). The organic phase was combined, dried with anhydrous sodium sulfate, filtered and concentrated to obtain the yellow solid title compound crude product 10 g, with a yield of 96%, which was directly put into the next step.

Step 3: 6-chloro-3-cyclobutyl pyrimidine-2,4(1H,3H)-dione

Phosphorus oxychloride (50 mL) was added into 1-cyclobutyl pyrimidine-2,4,6(1H,3H,5H)-trione (10 g, 54.89 mmol) and triethyl benzyl ammonium chloride (17.5 g, 76.84 mmol), the obtained reaction solution reacted at 50° C. for 3 hours, and then was concentrated under the reduced pressure. The residue was poured into ice water, stirred violently for 30 minutes, and then extracted by ethyl acetate (30 mL×2). The organic phase was combined, dried with anhydrous sodium sulfate, filtered and concentrated, and the obtained residue was purified by silica gel column chromatography (PE/EA (v/v)=2/1) to obtain a yellow solid title compound of 0.8 g, with a yield of 7.2%.

Step 4: (S)-3-cyclobutyl-6-((1-(phenyl-d5)ethyl)amino)pyrimidine-2,4(1H,3H)-dione Sodium hydroxide solution (20 mL, 1 M) was added into (S)-1-(phenyl-d5)ethane-1-amine hydrochloride (300 mg, 1.84 mmol) and stirred for 30 min. The reaction solution was extracted by ethyl acetate (30 mL×2), dried by anhydrous sodium sulfate, filtered, and concentrated under the reduced pressure. The obtained residue was added to a solution of 6-chloro-3-cyclobutyl pyrimidine-2,4(1H,3H)-dione (444 mg, 2.21 mmol) and 1,4-dioxane (10 mL), the reaction system was heated to 100° C. and stirred overnight. After the reaction was stopped and the reaction system was naturally cooled to room temperature, it was concentrated at reduced pressure. The obtained residue was purified by silica gel column chromatography (PE/EA (v/v)=1/1) to obtain a pale yellow solid title compound of 66 mg, with a yield of 12.3%.

MS (ESI, pos.ion) m/z: 291.2 [M+1]$^+$;

$^1$H NMR (400 MHz, DMSO-$d_6$) δ 9.87 (s, 1H), 6.55 (d, J=6.4 Hz, 1H), 5.17-5.03 (m, 1H), 4.57-4.44 (m, 1H), 4.34 (s, 1H), 2.90-2.79 (m, 2H), 2.01-1.93 (m, 2H), 1.76-1.65 (m, 1H), 1.65-1.53 (m, 1H), 1.40 (d, J=6.7 Hz, 3H).

Biological Test

Example A: Determination of Myosin Inhibition

Test Method and Procedure

Bovine myocardial myosin has ATPase activity. During the reaction, ATP is consumed to produce adenosine diphosphate (ADP) and free phosphorus ions are released. In the presence of phosphorus ions, purine nucleotide phosphorylase (PNP) catalyzes 2-amino-6-mercapto-7-methylpurine nucleoside (MESG) into 2-amino-6-mercapto-7-methylpurine, and the changes in absorbance can be detected at 355 nm.

Bovine myocardial myosin reaction system (0.0075 mg/mL bovine myocardial myosin, 0.25 mg/mL bovine myocardium fine myofilament complex, 0.6 μM ATP, 1× 2-amino-6-mercapto-7-methylpurine nucleoside, 1× purine nucleotide phosphorylase) was prepared under the condition of room temperature. The compound to be tested was mixed with the above bovine myosin reaction solution and incubated at room temperature for 30 minutes. After 30 minutes, 120 μM CaCl$_2$ was added to start the reaction, which was detected by using EnSpire (OD355 nM, 25° C.), which was read every 30 seconds for a total of 40 minutes. The Prism program (GraphPad) was used for data analysis.

The compound of the disclosure is tested according to the above method, and the experimental results are shown in Table 1.

TABLE 1

| The myosin inhibitory activity of the compound of the present disclosure | | |
|---|---|---|
| Compound | 2.5 μM (Inhibition rate) | 0.5 μM (Inhibition rate) |
| Example 1 | 48% | 9% |

Conclusion: the compound of the present disclosure has a high inhibitory rate on bovine myocardial myosin, indicating that the compound of the present disclosure can effectively inhibit myosin.

Example B Pharmacokinetic Test

1. Test Method

Experimental animals: 4 healthy adult male SD rats (purchased from Hunan SJA Laboratory Animal Co., Ltd) were divided into two groups, one for intravenous injection administration and three for orally intragastric administration.

Drug preparation: a certain amount of the compound of the present disclosure or MYK461 is weighted, and 10% DMSO, 10% Kolliphor HS15 and 80% saline are added to prepare the compound solution with target concentration.

Administration and sample collection: the animals fasted for 12 h before administration, ate in 3 h after administration, and were administered by intravenous administration (IV, 1 mg/kg) through the posterior limb vein of SD rats and orally intragastric administration (PO, 5 mg/kg), respectively. Then, blood samples were collected from the tail vein of rats at time points of 0, 0.083, 0.25, 0.5, 1, 2, 4, 6, 8, and 24 h, respectively, and the blood volume was about 200-400 μL/time point. After collecting whole blood at each time point, the blood samples were placed in K$_2$EDTA anticoagulant test tubes, which were placed in an incubator with ice packs for preservation. All the samples were centrifuged at 4600 r/min at 4° C. for 5 min within 15 min to obtain plasma. The concentrations of different compounds in rat plasma after administration were determined by LC/MS/MS method. Pharmacokinetic parameters were calculated according to the drug concentration-time curve.

The pharmacokinetic properties of the compound of the present disclosure were tested by the above tests. The test results showed that the compound of the disclosure had excellent pharmacokinetic characteristics in rats after intravenous injection administration or oral administration, that is, the compound of the disclosure had excellent pharmacokinetic properties. Specifically, the pharmacokinetic parameters in rats after intravenous injection administration are shown in Table 2.

2. Test Results

TABLE 2

| The pharmacokinetic properties of the compound of the present disclosure | | | | | | | | | | |
|---|---|---|---|---|---|---|---|---|---|---|
| Number | Mode of administration | Dosage (mg/kg) | AUC$_{INF}$ (h*ng/ml) | AUC$_{last}$ (h*ng/ml) | Cl (ml/min/kg) | C$_{max}$ (ng/ml) | MRT$_{INF}$ (h) | T$_{1/2}$ (h) | T$_{max}$ (h) | V$_{ss}$ (l/kg) |
| MYK461 | iv | 1 | 3090 | 2420 | 5.39 | 393 | 15.1 | 11.6 | 0.083 | 4.87 |
| Example 1 | iv | 1 | 6830 | 3670 | 2.44 | 883 | 31.1 | 22.6 | 0.083 | 4.56 |
| Example 2 | iv | 1 | 4670 | 3290 | 3.57 | 643 | 18.8 | 13.9 | 0.083 | 4.03 |
| Example 5 | iv | 1 | 5690 | 4450 | 2.93 | 982 | 14.8 | 11.3 | 0.083 | 2.6 |

Conclusion: as shown in Table 2, compared with MYK461, the levels of Cmax, $AUC_{INF}$ and $AUC_{last}$ in rats after intravenous administration of the compound of the disclosure are higher, the clearance rate of Cl is lower, and the half-life time of T½ is longer, and it has excellent pharmacokinetic characteristics.

In the description of this specification, reference term "an example", "an embodiment", "some examples", "sample", "specific example" or "some samples" and other description mean that the specific feature, structure, material or characteristic described in conjunction with the example, embodiment or example is included in at least one example, embodiment or example of the present disclosure. In this specification, the schematic representation of the above term is not necessary to be directed to the same example, embodiment or sample. Furthermore, the specific features, structures, materials or characteristics described may be combined in an appropriate manner in any one or more examples, embodiments or samples.

In addition, without contradiction, those skilled in the art could combine and integrate the different examples, embodiments or samples described in this specification, as well as the features of different examples, embodiments or samples.

Although examples of the present disclosure have been shown and described above, it is understood that the above examples are exemplary and not to be understood as limitations to the disclosure, and that ordinary technicians in the field could make changes, modifications, substitutions and variations to the above examples within the scope of the present disclosure.

What is claimed is:

1. A compound, wherein the compound is a compound represented by Formula I, or a stereoisomer, a geometric isomer, a tautomer, a hydrate, a solvate, or a pharmaceutical acceptable salt of the compound represented by Formula I,

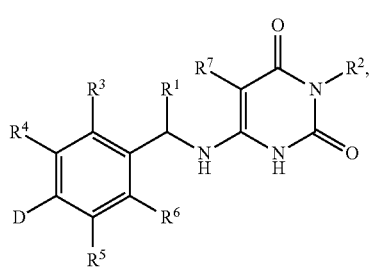

(I)

wherein
$R^1$ is selected from the group consisting of $C_{1-6}$ alkyl, $C_{3-8}$ cycloalkyl, heterocyclyl composed of 3-8 atoms, $C_{6-10}$ aryl and heteroaryl composed of 5-10 atoms, wherein the $C_{1-6}$ alkyl, $C_{3-8}$ cycloalkyl, heterocyclyl composed of 3-8 atoms, $C_{6-10}$ aryl and heteroaryl composed of 5-10 atoms are independently not substituted or substituted by 1, 2, 3, or 4 $R^x$, respectively;

$R^2$ is selected from the group consisting of $C_{1-6}$ alkyl, $C_{3-8}$ cycloalkyl, heterocyclyl composed of 3-8 atoms, $C_{6-10}$ aryl and heteroaryl composed of 5-10 atoms, wherein the $C_{1-6}$ alkyl, $C_{3-8}$ cycloalkyl, heterocyclyl composed of 3-8 atoms, $C_{6-10}$ aryl and heteroaryl composed of 5-10 atoms are independently not substituted or substituted by 1, 2, 3, or 4 $R^y$, respectively;

$R^3$, $R^4$, $R^5$ and $R^6$ are each independently selected from the group consisting of H, D, F, Cl, Br, I, CN, $NO_2$, OH, $NH_2$, SH, $C_{1-6}$ alkyl, $C_{1-6}$ haloalkyl, $C_{1-6}$ haloalkoxy, $C_{1-6}$ alkylamino, $C_{1-6}$ alkoxy, —C(=O)$R^g$, —C(=O)OR$^h$, —S(=O)$_2$R$^g$, —C(=O)NR$^i$R$^j$, —S(=O)$_2$NR$^i$R$^j$, $C_{3-8}$ cycloalkyl, heterocyclyl composed of 3-8 atoms, $C_{6-10}$ aryl and heteroaryl composed of 5-10 atoms, wherein OH, $NH_2$, SH, $C_{1-6}$ alkyl, $C_{1-6}$ haloalkyl, $C_{1-6}$ haloalkoxy, $C_{1-6}$ alkylamino, $C_{1-6}$ alkoxy, $C_{3-8}$ cycloalkyl, heterocyclyl composed of 3-8 atoms, $C_{6-10}$ aryl and heteroaryl composed of 5-10 atoms are independently not substituted or substituted by 1, 2, 3, or 4 $R^z$, respectively; and $R^7$ is selected from the group consisting of H, D, F, Cl, Br, I, $C_{1-6}$ alkyl and $C_{1-6}$ haloalkyl, wherein $R^x$, $R^y$ and $R^z$ are each independently selected from the group consisting of D, F, Cl, Br, I, CN, $NO_2$, OH, $NH_2$, SH, $C_{1-6}$ alkyl, $C_{1-6}$ haloalkyl, $C_{1-6}$ alkylamino, $C_{3-8}$ cycloalkyl, heterocyclyl composed of 3-8 atoms, $C_{6-10}$ aryl, heteroaryl composed of 5-10 atoms, —(CR$^a$R$^b$)$_n$R$^o$, —OR$^c$, —C(=O)R$^d$, —C(=O)OR$^c$, —S(=O)$_2$R$^d$, —C(=O)NR$^e$R$^f$ and —S(=O)$_2$NR$^e$R$^f$, wherein $R^a$ and $R^b$ are each independently selected from the group consisting of H, $C_{1-6}$ alkyl and $C_{1-6}$ haloalkyl;

$R^o$ is each independently selected from the group consisting of $C_{3-8}$ cycloalkyl, heterocyclyl composed of 3-8 atoms, $C_{6-10}$ aryl and heteroaryl composed of 5-10 atoms;

$R^c$, $R^e$, $R^f$, $R^h$, $R^i$ and $R^j$ are each independently selected from the group consisting of H, D, $C_{1-6}$ alkyl, $C_{1-6}$ haloalkyl, $C_{3-8}$ cycloalkyl, heterocyclyl composed of 3-8 atoms, $C_{6-10}$ aryl and heteroaryl composed of 5-10 atoms; or $R^e$, $R^f$ and a nitrogen atom attached to them form a heterocyclyl composed of 3-8 atoms or a heteroaryl composed of 5-10 atoms;

$R^d$ and $R^g$ are each independently selected from the group consisting of H, OH, $NH_2$, $C_{1-6}$ alkyl, $C_{1-6}$ haloalkyl, $C_{1-6}$ alkylamino, $C_{1-6}$ alkoxy, $C_{3-8}$ cycloalkyl, heterocyclyl composed of 3-8 atoms, $C_{6-10}$ aryl and heteroaryl composed of 5-10 atoms; and n is each independently 1, 2, 3 or 4.

2. The compound according to claim 1, wherein the compound is a compound represented by Formula II, or a stereoisomer, a geometric isomer, a tautomer, a hydrate, a solvate, or a pharmaceutical acceptable salt of the compound represented by Formula II,

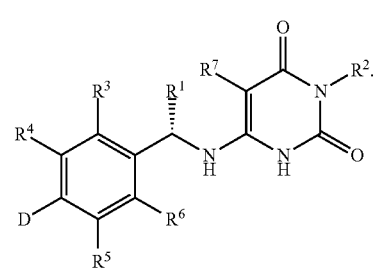

(II)

3. The compound according to claim 1, wherein $R^1$ is selected from the group consisting of $C_{1-4}$ alkyl, $C_{3-6}$ cycloalkyl, heterocyclyl composed of 3-6 atoms, phenyl and heteroaryl composed of 5-6 atoms, wherein the $C_{1-4}$ alkyl, $C_{3-6}$ cycloalkyl, heterocyclyl composed of 3-6 atoms, phenyl and heteroaryl composed of 5-6 atoms are independently not substituted or substituted by 1, 2, 3, or 4 $R^x$, respectively;

$R^3$, $R^4$, $R^5$ and $R^6$ are each independently selected from the group consisting of H, D, F, Cl, Br, I, CN, $NO_2$, OH, $NH_2$, SH, $C_{1-4}$ alkyl, $C_{1-4}$ haloalkyl, $C_{1-4}$ haloalkoxy, $C_{1-4}$ alkylamino, $C_{1-4}$ alkoxy, —C(=O)R$^g$, —C(=O)OR$^h$, —S(=O)$_2$R$^g$, —C(=O)NR$^i$R$^j$, —S(=O)$_2$NR$^i$R$^j$, $C_{3-6}$ cycloalkyl, heterocyclyl composed of 3-6 atoms, $C_{6-10}$ aryl and heteroaryl composed of 5-6 atoms, wherein OH, NH$_2$, SH, $C_{1-4}$ alkyl, $C_{1-4}$ haloalkyl, $C_{1-4}$ haloalkoxy, $C_{1-4}$ alkylamino, $C_{1-4}$ alkoxy, $C_{3-6}$ cycloalkyl, heterocyclyl composed of 3-6 atoms, $C_{6-10}$ aryl and heteroaryl composed of 5-6 atoms are independently not substituted or substituted by 1, 2, 3, or 4 R$^z$, respectively; and R$^7$ is selected from the group consisting of H, D, F, Cl, Br, I, $C_{1-4}$ alkyl and $C_{1-4}$ haloalkyl.

4. The compound according to claim 1, wherein R$^2$ is selected from the group consisting of $C_{1-4}$ alkyl, $C_{3-6}$ cycloalkyl, heterocyclyl composed of 3-6 atoms, phenyl and heteroaryl composed of 5-6 atoms, wherein the $C_{1-4}$ alkyl, $C_{3-6}$ cycloalkyl, heterocyclyl composed of 3-6 atoms, phenyl and heteroaryl composed of 5-6 atoms are independently not substituted or substituted by 1, 2, 3, or 4 R$^y$, respectively.

5. The compound according to claim 1, wherein R$^1$ is selected from the group consisting of methyl, ethyl, n-propyl, isopropyl, n-butyl, tent-butyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl, wherein methyl, ethyl, n-propyl, isopropyl, n-butyl, tent-butyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl are independently not substituted or substituted by 1, 2, 3, or 4 R$^x$, respectively;

R$^3$, R$^4$, R$^5$ and R$^6$ are each independently selected from the group consisting of H, D, F, Cl, Br, I, CN, NO$_2$, OH, NH$_2$, SH, methyl, ethyl, n-propyl, isopropyl, n-butyl, tent-butyl, trifluoromethyl, trifluoromethoxy, methylamino, dimethylamino, methoxyl, ethyoxyl, —C(=O)R$^g$, —C(=O)OR$^h$, —S(=O)$_2$R$^g$, —C(=O)NR$^i$R$^j$, —S(=O)$_2$NR$^i$R$^j$, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl, wherein OH, NH$_2$, SH, methyl, ethyl, n-propyl, isopropyl, n-butyl, tent-butyl, methylamino, dimethylamino, methoxyl, ethyoxyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl are independently not substituted or substituted by 1, 2, 3, or 4 R$^z$, respectively; and R$^7$ is selected from the group consisting of H, D, F, Cl and Br.

6. The compound according to claim 1, wherein R$^2$ is selected from the group consisting of methyl, ethyl, n-propyl, isopropyl, n-butyl, 1-methylpropyl, tent-butyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl, wherein methyl, ethyl, n-propyl, isopropyl, n-butyl, tent-butyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl are independently not substituted or substituted by 1, 2, 3, or 4 R$^y$, respectively.

7. The compound according to claim 1, wherein R$^x$, R$^y$ and R$^z$ are each independently selected from the group consisting of D, F, Cl, Br, I, CN, NO$_2$, OH, NH$_2$, —SH, $C_{1-4}$ alkyl, $C_{1-4}$ haloalkyl, $C_{1-4}$ alkylamino, $C_{3-6}$ cycloalkyl, heterocyclyl composed of 3-6 atoms, phenyl, heteroaryl composed of 5-6 atoms, —(CR$^a$R$^b$)$_n$R$^0$, —OR$^c$, —C(=O)R$^d$, —C(=O)OR$^e$, —S(=O)$_2$R$^d$, —C(=O)NR$^e$R$^f$ and —S(=O)NR$^e$R$^f$, wherein R$^a$ and R$^b$ are each independently selected from the group consisting of H, $C_{1-4}$ alkyl and $C_{1-4}$ haloalkyl;

R$^0$ is each independently selected from the group consisting of $C_{3-6}$ cycloalkyl, heterocyclyl composed of 3-6 atoms, phenyl and heteroaryl composed of 5-6 atoms;

R$^c$, R$^e$, R$^f$, R$^h$, R$^i$ and R$^j$ are each independently selected from the group consisting of H, D, $C_{1-4}$ alkyl, $C_{1-4}$ haloalkyl, $C_{3-6}$ cycloalkyl, heterocyclyl composed of 3-6 atoms, phenyl and heteroaryl composed of 5-6 atoms; or R$^e$, R$^f$ and a nitrogen atom attached to them form a heterocyclyl composed of 3-6 atoms or a heteroaryl composed of 5-6 atoms;

R$^d$ and R$^g$ are each independently selected from the group consisting of H, OH, NH$_2$, $C_{1-4}$ alkyl, $C_{1-4}$ haloalkyl, $C_{1-4}$ alkylamino, $C_{1-4}$ alkoxy, $C_{3-6}$ cycloalkyl, heterocyclyl composed of 3-6 atoms, phenyl and heteroaryl composed of 5-6 atoms; and n is each independently 1, 2, 3 or 4.

8. The compound according to claim 1, wherein R$^x$, R$^y$ and R$^z$ are each independently selected from the group consisting of D, F, Cl, Br, I, CN, NO$_2$, OH, NH$_2$, —SH, methyl, ethyl, n-propyl, isopropyl, n-butyl, tent-butyl, trifluoromethyl, difluoromethyl, methylamino, dimethylamino, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl, pyridazinyl, —(CR$^a$R$^b$)$_n$R$^0$, —OR$^c$, —C(=O)R$^d$, —C(=O)OR$^e$, —S(=O)$_2$R$^d$, —C(=O)NR$^e$R$^f$ and —S(=O)$_2$NR$^e$R$^f$, wherein R$^a$ and R$^b$ are each independently selected from the group consisting of H, methyl, ethyl, n-propyl, isopropyl, n-butyl, tent-butyl and trifluoromethyl;

R$^0$ is each independently selected from the group consisting of cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl;

$R^c$, $R^e$, $R^f$, $R^h$, $R^i$ and $R^j$ and are each independently selected from the group consisting of H, D, methyl, ethyl, n-propyl, isopropyl, n-butyl, tent-butyl, trifluoromethyl, difluoromethyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl; or $R^e$, $R^f$ and a nitrogen atom attached to them form a heterocyclyl composed of 3-6 atoms or a heteroaryl composed of 5-6 atoms;

$R^d$ and $R^g$ are each independently selected from the group consisting of H, OH, $NH_2$, methyl, ethyl, n-propyl, isopropyl, n-butyl, tent-butyl, trifluoromethyl, difluoromethyl, methylamino, dimethylamino, methoxyl, ethyoxyl, cyclopropyl, cyclobutyl, cyclopentyl, cyclohexyl, epoxyethyl, azacyclobutyl, oxacyclobutyl, tetrahydrofuranyl, tetrahydrothienyl, tetrahydropyranyl, pyrrolidinyl, pyrazolidyl, imidazolidinyl, piperidyl, morpholinyl, piperazinyl, phenyl, pyrrolyl, pyrazolyl, thienyl, thiazolyl, furyl, imidazolyl, oxazolyl, triazolyl, tetrazolyl, isoxazolyl, pyridyl, pyrimidinyl, pyrazinyl and pyridazinyl; and n is each independently 1, 2, 3 or 4.

9. A compound, wherein the compound is a compound in one of following structures, or a stereoisomer, a geometric isomer, a tautomer, a hydrate, a solvate, or a pharmaceutical acceptable salt of the compound in one of following structures:

001

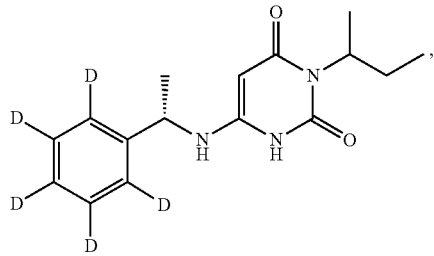

002

003

-continued

004

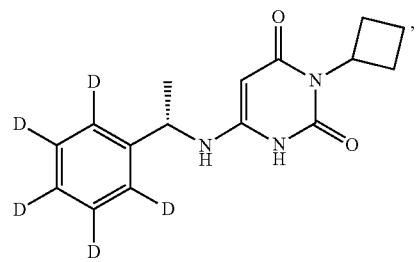

005

006

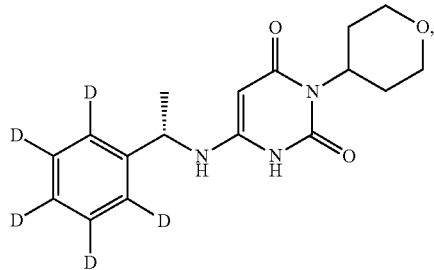

007

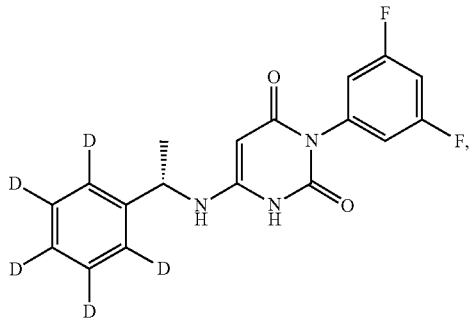

008

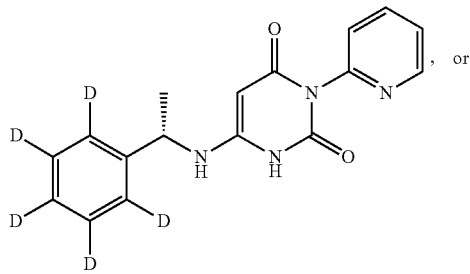

-continued
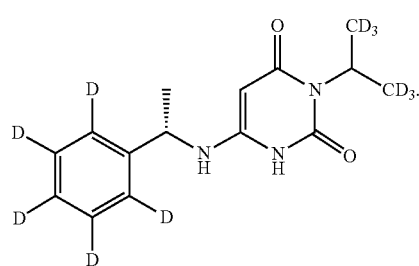
009
10. A pharmaceutical composition, comprising the compound according to claim 1 and a pharmaceutically acceptable excipient, carrier, adjuvant or any combination thereof.
* * * * *